(12) United States Patent
Minvielle

(10) Patent No.: US 9,877,504 B2
(45) Date of Patent: *Jan. 30, 2018

(54) CONDITIONING SYSTEM FOR NUTRITIONAL SUBSTANCES

(71) Applicant: Iceberg Luxembourg S.A.R.L., Luxembourg (LU)

(72) Inventor: Eugenio Minvielle, Hillsborough, CA (US)

(73) Assignee: Iceberg Luxembourg S.A.R.L., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/482,656

(22) Filed: Apr. 7, 2017

(65) Prior Publication Data

US 2017/0208850 A1 Jul. 27, 2017

Related U.S. Application Data

(60) Division of application No. 13/602,040, filed on Aug. 31, 2012, now Pat. No. 9,619,781, which is a (Continued)

(51) Int. Cl.
*A23P 10/00* (2016.01)
*G06Q 10/10* (2012.01)
(Continued)

(52) U.S. Cl.
CPC .............. *A23P 10/00* (2016.08); *A23L 5/00* (2016.08); *G05B 15/02* (2013.01); *G06Q 10/10* (2013.01); *A23V 2002/00* (2013.01)

(58) Field of Classification Search
CPC ...... H05B 6/6447; H05B 6/647; H05B 6/687; H05B 6/688; A23L 1/00; A23L 3/00; A23P 1/00; Y02B 40/143
(Continued)

(56) References Cited

U.S. PATENT DOCUMENTS 3,685,308 A  8/1972 Lundquist
4,225,410 A  9/1980 Pace
(Continued)

FOREIGN PATENT DOCUMENTS

CN  101118425 A  2/2008
CN  101173316 A  5/2008
(Continued)

OTHER PUBLICATIONS

Office Action in U.S. Appl. No. 13/485,854, dated Nov. 4, 2016.
(Continued)

*Primary Examiner* — Shogo Sasaki
(74) *Attorney, Agent, or Firm* — Nixon Peabody LLP

(57) ABSTRACT

Disclosed herein is a conditioning system for nutritional substances. The conditioning system obtains information regarding the nutritional substance to be conditioned, the desired conditioning, and the desired properties, including nutritional content, of the conditioned nutritional substance, and dynamically controls the conditioning in response to this information optimize the organoleptic properties of the conditioned nutritional substance, while minimizing any detrimental changes to the nutritional content.

3 Claims, 6 Drawing Sheets

Related U.S. Application Data continuation of application No. 13/485,866, filed on May 31, 2012.

(60) Provisional application No. 61/624,788, filed on Apr. 16, 2012, provisional application No. 61/624,745, filed on Apr. 16, 2012, provisional application No. 61/624,765, filed on Apr. 16, 2012.

(51) Int. Cl.
  *G05B 15/02* (2006.01)
  *A23L 5/00* (2016.01)

(58) Field of Classification Search
  USPC ........ 700/266, 9, 28; 702/19, 22, 23, 30–32;
  99/275, 325, 337, 468, 486; 426/231,
  426/278
  See application file for complete search history.

(56) References Cited

U.S. PATENT DOCUMENTS

| | | |
|---|---|---|
| 4,555,930 A | 12/1985 | Leach et al. |
| 4,644,137 A | 2/1987 | Asahi et al. |
| 4,644,154 A | 2/1987 | Brogardh et al. |
| 4,650,766 A | 3/1987 | Harm et al. |
| 4,674,320 A | 6/1987 | Hirschfeld |
| 4,777,599 A | 10/1988 | Dorogi et al. |
| 4,831,239 A | 5/1989 | Ueda |
| 4,837,035 A | 6/1989 | Baker et al. |
| 4,874,928 A | 10/1989 | Kasai |
| 4,914,277 A | 4/1990 | Guerin et al. |
| 5,034,242 A | 7/1991 | Lasdon et al. |
| 5,062,066 A | 10/1991 | Scher et al. |
| D333,782 S | 3/1993 | van Berlo |
| 5,250,789 A | 10/1993 | Johnsen |
| 5,361,681 A | 11/1994 | Hedström |
| 5,412,560 A | 5/1995 | Dennision |
| 5,442,669 A | 8/1995 | Medin |
| 5,478,900 A | 12/1995 | Amano et al. |
| 5,478,989 A | 12/1995 | Shepley |
| 5,478,990 A | 12/1995 | Montanari et al. |
| 5,496,576 A | 5/1996 | Jeong |
| 5,553,609 A | 9/1996 | Chen et al. |
| 5,558,797 A | 9/1996 | Takagi |
| 5,673,691 A | 10/1997 | Abrams et al. |
| 5,697,177 A | 12/1997 | Ludlow et al. |
| 5,804,803 A | 9/1998 | Cragun et al. |
| 5,853,790 A | 12/1998 | Glancy |
| 5,872,721 A | 2/1999 | Huston et al. |
| 5,877,477 A | 3/1999 | Petty et al. |
| 5,954,640 A | 9/1999 | Szabo |
| 6,012,415 A | 1/2000 | Linseth |
| 6,080,972 A | 6/2000 | May |
| 6,119,531 A | 9/2000 | Wendte et al. |
| 6,182,725 B1 | 2/2001 | Sorvik |
| 6,211,789 B1 | 4/2001 | Oldham et al. |
| 6,270,724 B1 | 8/2001 | Woodaman |
| 6,276,264 B1 | 8/2001 | Dumm |
| 6,285,282 B1 | 9/2001 | Dorenbosch et al. |
| 6,299,920 B1 | 10/2001 | Saskena |
| 6,299,921 B1 | 10/2001 | Loffler et al. |
| 6,308,116 B1 | 10/2001 | Ricks et al. |
| 6,310,964 B1 | 10/2001 | Mohan et al. |
| 6,325,878 B1 | 12/2001 | Borgstrom |
| 6,356,940 B1 | 3/2002 | Short |
| 6,387,049 B1 | 5/2002 | Moore |
| 6,444,233 B1 | 9/2002 | Arntzen et al. |
| 6,483,434 B1 | 11/2002 | Umiker |
| 6,491,217 B2 | 12/2002 | Catan |
| 6,502,411 B2 | 1/2003 | Okamoto |
| 6,512,919 B2 | 1/2003 | Ogasawara |
| 6,513,532 B2 | 2/2003 | Mault et al. |
| 6,538,215 B2 | 3/2003 | Montagnino et al. |
| 6,549,818 B1 | 4/2003 | Ali |
| 6,553,386 B1 | 4/2003 | Alabaster |
| 6,554,182 B1 | 4/2003 | Magnusson et al. |
| 6,556,963 B1 | 4/2003 | Tetzlaff |
| 6,571,603 B1 | 6/2003 | Doleman et al. |
| D478,773 S | 8/2003 | Palen |
| 6,616,047 B2 | 9/2003 | Catan |
| 6,631,333 B1 | 10/2003 | Lewis et al. |
| 6,671,698 B2 | 12/2003 | Pickett et al. |
| 6,676,014 B2 | 1/2004 | Catan |
| 6,689,398 B2 | 2/2004 | Haridas et al. |
| 6,691,135 B2 | 2/2004 | Pickett et al. |
| 6,716,462 B2 | 4/2004 | Prosise et al. |
| 6,759,635 B2 | 7/2004 | Lile |
| 6,773,926 B1 | 8/2004 | Freund et al. |
| 6,789,021 B2 | 9/2004 | Rendahl et al. |
| 6,809,301 B1 | 10/2004 | McIntyre et al. |
| 6,844,197 B1 | 1/2005 | Doleman et al. |
| 6,862,494 B2 | 3/2005 | Hu et al. |
| 6,874,000 B2 | 3/2005 | Sholl et al. |
| 6,888,458 B2 | 5/2005 | Carlson |
| 6,953,342 B2 | 10/2005 | Bisogno |
| 6,953,919 B2 | 10/2005 | Clothier |
| 6,975,910 B1 | 12/2005 | Brown et al. |
| 6,982,640 B2 | 1/2006 | Lindsay et al. |
| 7,024,369 B1 | 4/2006 | Brown et al. |
| 7,076,438 B1 | 7/2006 | Tobelmann et al. |
| 7,080,593 B1 | 7/2006 | Frankel |
| 7,085,777 B2 | 8/2006 | Beck et al. |
| 7,090,638 B2 | 8/2006 | Vidgen |
| 7,103,481 B2 | 9/2006 | Negri |
| 7,151,447 B1 | 12/2006 | Willms et al. |
| 7,152,040 B1 | 12/2006 | Hawthorne et al. |
| D534,758 S | 1/2007 | Lee et al. |
| D539,072 S | 3/2007 | Kawata et al. |
| D539,595 S | 4/2007 | Okuda et al. |
| D540,613 S | 4/2007 | Jeon |
| D541,578 S | 5/2007 | Jeon |
| 7,212,955 B2 | 5/2007 | Kirshenbaum et al. |
| 7,213,743 B2 | 5/2007 | Carlson et al. |
| 7,215,420 B2 | 5/2007 | Gellerman et al. |
| 7,237,400 B2 | 7/2007 | Owada |
| 7,256,699 B2 | 8/2007 | Tethrake et al. |
| 7,275,863 B1 | 10/2007 | Akers et al. |
| 7,295,889 B2 | 11/2007 | Lahteenmaki |
| D560,960 S | 2/2008 | Hillmann et al. |
| 7,326,888 B2 | 2/2008 | Chun et al. |
| 7,349,857 B2 | 3/2008 | Manzo |
| 7,357,316 B2 | 4/2008 | Heckel et al. |
| 7,359,802 B1 | 4/2008 | Lewis et al. |
| 7,372,003 B2 | 5/2008 | Kates |
| 7,396,550 B2 | 7/2008 | Angel |
| 7,403,855 B2 | 7/2008 | Fuessley et al. |
| 7,440,901 B1 | 10/2008 | Dlott et al. |
| 7,445,372 B1 | 11/2008 | Engel et al. |
| 7,474,965 B2 | 1/2009 | Johnson et al. |
| 7,532,106 B2 | 5/2009 | Debord et al. |
| 7,571,676 B2 | 8/2009 | Nelson et al. |
| 7,620,531 B1 | 11/2009 | Johnson |
| D607,264 S | 1/2010 | Lee |
| 7,681,383 B2 | 3/2010 | Argetsinger et al. |
| 7,809,601 B2 | 5/2010 | Shaya et al. |
| D618,488 S | 6/2010 | Knochner |
| 7,743,591 B2 | 6/2010 | Meier et al. |
| 7,797,204 B2 | 9/2010 | Balent |
| 7,836,876 B2 | 11/2010 | Schellenberg |
| 7,840,359 B2 | 11/2010 | Hsiung et al. |
| 7,854,108 B2 | 12/2010 | Koselka et al. |
| D633,326 S | 3/2011 | Shin et al. |
| 7,933,733 B2 | 4/2011 | Ashrafzadeh et al. |
| 7,942,867 B2 | 5/2011 | Hood et al. |
| 7,951,079 B1 | 5/2011 | Moore |
| 7,957,850 B2 | 6/2011 | Anderson |
| 7,996,134 B2 | 8/2011 | Roberts |
| 8,009,048 B2 | 8/2011 | Hyde et al. |
| 8,033,237 B2 | 10/2011 | Havens et al. |
| 8,082,809 B2 | 12/2011 | Luellen et al. |
| D654,299 S | 2/2012 | Benold |
| 8,112,303 B2 | 2/2012 | Eglen et al. |
| 8,140,381 B1 | 3/2012 | Wu et al. |

(56) References Cited

U.S. PATENT DOCUMENTS

| | | |
|---|---|---|
| D657,607 S | 4/2012 | Ohmae et al. |
| 8,147,888 B2 | 4/2012 | Kling et al. |
| 8,173,188 B2 | 5/2012 | Suetsugu |
| 8,193,474 B2 | 6/2012 | Harris |
| D665,220 S | 8/2012 | Ohmae et al. |
| 8,285,593 B2 | 10/2012 | Bhatt et al. |
| 8,314,701 B2 | 11/2012 | Grieco et al. |
| D673,001 S | 12/2012 | Becze et al. |
| 8,393,137 B1 | 3/2013 | Crosby |
| 8,403,215 B2 | 3/2013 | Aihara et al. |
| 8,490,862 B1 | 7/2013 | Minvielle |
| 8,550,365 B1 | 10/2013 | Minvielle |
| 8,626,796 B2 | 1/2014 | McBride et al. |
| 8,631,050 B1 | 1/2014 | Gayle |
| 8,668,140 B2 | 3/2014 | Minvielle |
| D702,482 S | 4/2014 | Davis et al. |
| 8,788,341 B1 | 7/2014 | Patel |
| 8,796,510 B2 | 8/2014 | Heard et al. |
| 8,825,516 B2 | 9/2014 | Grant et al. |
| 9,016,193 B2 | 4/2015 | Minvielle |
| 2002/0004749 A1 | 1/2002 | Froseth et al. |
| 2002/0005412 A1 | 1/2002 | Laforcade |
| 2002/0011567 A1 | 1/2002 | Ozanich |
| 2002/0040564 A1 | 4/2002 | Killingbeck et al. |
| 2002/0059175 A1 | 5/2002 | Nakano |
| 2002/0085164 A1 | 7/2002 | Stanford-Clark |
| 2002/0091593 A1 | 7/2002 | Fowler |
| 2002/0106432 A1 | 8/2002 | Yamagata et al. |
| 2002/0123070 A1 | 9/2002 | Hsieh |
| 2002/0125313 A1 | 9/2002 | Broff |
| 2002/0134778 A1 | 9/2002 | Day et al. |
| 2002/0163436 A1 | 11/2002 | Singh et al. |
| 2002/0168456 A1 | 11/2002 | Robbins |
| 2003/0006281 A1 | 1/2003 | Thomas et al. |
| 2003/0027161 A1 | 2/2003 | Bejanin et al. |
| 2003/0050730 A1 | 3/2003 | Greeven et al. |
| 2003/0099157 A1 | 5/2003 | Quine |
| 2003/0136960 A1 | 7/2003 | Goodman et al. |
| 2003/0163354 A1 | 8/2003 | Shamoun |
| 2003/0165602 A1 | 9/2003 | Garwood |
| 2003/0185937 A1 | 10/2003 | Garwood |
| 2003/0185948 A1 | 10/2003 | Garwood |
| 2003/0204359 A1 | 10/2003 | Blakley et al. |
| 2003/0227392 A1 | 12/2003 | Ebert et al. |
| 2004/0045202 A1 | 3/2004 | Arrendale, III et al. |
| 2004/0083201 A1 | 4/2004 | Sholl et al. |
| 2004/0093274 A1 | 5/2004 | Vanska et al. |
| 2004/0100380 A1 | 5/2004 | Lindsay et al. |
| 2004/0130714 A1 | 7/2004 | Gellerman et al. |
| 2004/0147038 A1 | 7/2004 | Lewis et al. |
| 2004/0148117 A1 | 7/2004 | Kirshenbaum et al. |
| 2004/0152131 A1 | 8/2004 | Hsieh |
| 2004/0158447 A1 | 8/2004 | Leger et al. |
| 2004/0167724 A1 | 8/2004 | Federer et al. |
| 2004/0191382 A1 | 9/2004 | Cooper et al. |
| 2004/0201454 A1 | 10/2004 | Waterhouse et al. |
| 2004/0215402 A1 | 10/2004 | Hsiung et al. |
| 2004/0261280 A1 | 12/2004 | Znaiden et al. |
| 2004/0267098 A1 | 12/2004 | Moore |
| 2005/0001728 A1 | 1/2005 | Appelt et al. |
| 2005/0027726 A1 | 2/2005 | Guivarch et al. |
| 2005/0049920 A1 | 3/2005 | Day et al. |
| 2005/0075900 A1 | 4/2005 | Arguimbau, III |
| 2005/0079491 A1 | 4/2005 | Donne-Gousse et al. |
| 2005/0106103 A1 | 5/2005 | Dussaud et al. |
| 2005/0168325 A1 | 8/2005 | Lievre et al. |
| 2005/0171738 A1 | 8/2005 | Kadaba |
| 2005/0184148 A1 | 8/2005 | Perlman |
| 2005/0247213 A1 | 11/2005 | Slilaty |
| 2005/0248455 A1 | 11/2005 | Pope et al. |
| 2005/0251449 A1 | 11/2005 | Pape et al. |
| 2006/0006173 A1 | 1/2006 | Kim et al. |
| 2006/0015371 A1 | 1/2006 | Knauf et al. |
| 2006/0061454 A1 | 3/2006 | Debord et al. |
| 2006/0062835 A1 | 3/2006 | Weil |
| 2006/0065263 A1 | 3/2006 | Barritt |
| 2006/0073483 A1 | 4/2006 | White et al. |
| 2006/0078658 A1 | 4/2006 | Owens et al. |
| 2006/0099310 A1 | 5/2006 | Koekkoek |
| 2006/0130498 A1 | 6/2006 | Joshi et al. |
| 2006/0172048 A1 | 8/2006 | Etchells et al. |
| 2006/0178841 A1 | 8/2006 | Fernandez |
| 2006/0200480 A1 | 9/2006 | Harris et al. |
| 2006/0201432 A1 | 9/2006 | Pratt |
| 2006/0251785 A1 | 9/2006 | Fraccon et al. |
| 2006/0228428 A1 | 10/2006 | Kang et al. |
| 2006/0240174 A1 | 10/2006 | Jung et al. |
| 2006/0256132 A1 | 11/2006 | Shin et al. |
| 2006/0277064 A1 | 12/2006 | Cannata |
| 2006/0286211 A1 | 12/2006 | Lang |
| 2007/0016852 A1 | 1/2007 | Kim et al. |
| 2007/0036840 A1 | 2/2007 | Tuduri et al. |
| 2007/0049910 A1 | 3/2007 | Altshuler et al. |
| 2007/0055551 A1 | 3/2007 | Szabo |
| 2007/0055573 A1 | 3/2007 | Grell |
| 2007/0059402 A1 | 3/2007 | Barmore |
| 2007/0118394 A1 | 5/2007 | Cahoon |
| 2007/0191689 A1 | 8/2007 | Elitok |
| 2007/0204691 A1 | 9/2007 | Bogner et al. |
| 2007/0207242 A1 | 9/2007 | Carlsen |
| 2007/0209656 A1 | 9/2007 | Lee |
| 2007/0254080 A1 | 11/2007 | Schackmuith et al. |
| 2007/0258048 A1 | 11/2007 | Pitchers |
| 2007/0269557 A1 | 11/2007 | Culver et al. |
| 2007/0294129 A1 | 12/2007 | Froseth et al. |
| 2007/0298147 A1 | 12/2007 | Haus |
| 2008/0058783 A1 | 3/2008 | Altshuler et al. |
| 2008/0059342 A1 | 3/2008 | Culver et al. |
| 2008/0077455 A1 | 3/2008 | Gilboa |
| 2008/0083825 A1 | 4/2008 | Yang et al. |
| 2008/0091705 A1 | 4/2008 | McBride et al. |
| 2008/0102175 A1 | 5/2008 | Jean et al. |
| 2008/0158543 A1 | 7/2008 | Puskas et al. |
| 2008/0162186 A1 | 7/2008 | Jones |
| 2008/0171120 A1 | 7/2008 | Willett |
| 2008/0183588 A1 | 7/2008 | Agrawal et al. |
| 2008/0186175 A1 | 8/2008 | Stern |
| 2008/0193614 A1 | 8/2008 | Greiner et al. |
| 2008/0195456 A1 | 8/2008 | Fitzpatrick et al. |
| 2008/0254449 A1 | 10/2008 | Plante |
| 2008/0275309 A1 | 11/2008 | Stivoric et al. |
| 2008/0280000 A1 | 11/2008 | Breunig et al. |
| 2008/0295702 A1 | 12/2008 | Wiedemann et al. |
| 2009/0029014 A1 | 1/2009 | Walter et al. |
| 2009/0035392 A1 | 2/2009 | Wilkinson |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0157460 A1 | 6/2009 | Narayanaswamy |
| 2009/0177068 A1 | 7/2009 | Stivoric et al. |
| 2009/0202700 A1 | 8/2009 | Bunke et al. |
| 2009/0208607 A1 | 8/2009 | Bunke et al. |
| 2009/0232958 A1 | 9/2009 | Samoto et al. |
| 2009/0236333 A1 | 9/2009 | Ben-Shmuel et al. |
| 2009/0236334 A1 | 9/2009 | Ben-Shmuel et al. |
| 2009/0275002 A1 | 11/2009 | Hoggle |
| 2009/0276912 A1 | 11/2009 | Sherman et al. |
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2010/0015313 A1 | 1/2010 | Harris |
| 2010/0055259 A1 | 3/2010 | Bourg, Jr. |
| 2010/0055653 A1 | 3/2010 | Miller-Kovach et al. |
| 2010/0075436 A1 | 3/2010 | Urdea et al. |
| 2010/0076585 A1 | 3/2010 | Mayer et al. |
| 2010/0076942 A1 | 3/2010 | Lee |
| 2010/0086655 A1 | 4/2010 | Singer |
| 2010/0097193 A1 | 4/2010 | Tang |
| 2010/0102959 A1 | 4/2010 | Ashrafzadeh et al. |
| 2010/0106625 A1 | 4/2010 | McCoy |
| 2010/0106626 A1 | 4/2010 | Ashrafzadeh et al. |
| 2010/0115785 A1 | 5/2010 | Ben-Shmuel et al. |

(56) References Cited

U.S. PATENT DOCUMENTS

| | | |
|---|---|---|
| 2010/0117819 A1 | 5/2010 | Murray |
| 2010/0119659 A1 | 5/2010 | Ovadia et al. |
| 2010/0125419 A1 | 5/2010 | Hyde et al. |
| 2010/0135211 A1 | 6/2010 | Park et al. |
| 2010/0152687 A1 | 6/2010 | Carlozzi |
| 2010/0175886 A1 | 7/2010 | Bohacs et al. |
| 2010/0185064 A1 | 7/2010 | Bandic et al. |
| 2010/0186600 A1 | 7/2010 | Lewis et al. |
| 2010/0198605 A1 | 8/2010 | Saulet |
| 2010/0199854 A1 | 8/2010 | Homme et al. |
| 2010/0210745 A1 | 8/2010 | McDaniel et al. |
| 2010/0213187 A1 | 8/2010 | Bandholz et al. |
| 2010/0216098 A1 | 8/2010 | Montgomery |
| 2010/0216136 A1 | 8/2010 | B.Che Man et al. |
| 2010/0218044 A1 | 8/2010 | Roblett et al. |
| 2010/0228160 A1 | 9/2010 | Schweizer |
| 2010/0264205 A1 | 10/2010 | Iida |
| 2010/0268658 A1 | 10/2010 | Medo et al. |
| 2010/0280895 A1 | 11/2010 | Mottola |
| 2010/0281636 A1 | 11/2010 | Ortins et al. |
| 2010/0287057 A1 | 11/2010 | Aihara et al. |
| 2010/0287101 A1 | 11/2010 | Ishikawa et al. |
| 2011/0029364 A1 | 2/2011 | Roeding et al. |
| 2011/0055044 A1 | 3/2011 | Wiedl |
| 2011/0082711 A1 | 4/2011 | Poeze et al. |
| 2011/0123689 A1 | 5/2011 | Luckhart et al. |
| 2011/0124096 A1 | 5/2011 | Philipak et al. |
| 2011/0151072 A1 | 6/2011 | Anderson et al. |
| 2011/0197827 A1 | 8/2011 | Chang |
| 2011/0204137 A1* | 8/2011 | Scharfenort et al. ......... 235/375 |
| 2011/0217205 A1 | 9/2011 | Peeters |
| 2011/0236862 A1 | 9/2011 | Culver et al. |
| 2011/0253693 A1 | 10/2011 | Lyons et al. |
| 2011/0257496 A1 | 10/2011 | Terashima et al. |
| 2011/0258130 A1 | 10/2011 | Grabiner et al. |
| 2011/0259953 A1 | 10/2011 | Baarman et al. |
| 2011/0259960 A1 | 10/2011 | Baarman et al. |
| 2011/0276402 A1 | 11/2011 | Boone |
| 2011/0301441 A1 | 12/2011 | Bandic et al. |
| 2011/0302050 A1 | 12/2011 | Kildevald |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0009550 A1 | 1/2012 | Gayle |
| 2012/0016814 A1 | 1/2012 | Evans |
| 2012/0027897 A1 | 2/2012 | Innocenzi |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0097050 A1 | 4/2012 | Schaefer et al. |
| 2012/0105424 A1 | 5/2012 | Lee et al. |
| 2012/0135455 A1 | 5/2012 | Nerin De La Puerta et al. |
| 2012/0152406 A1 | 6/2012 | Bartholomew et al. |
| 2012/0169469 A1 | 7/2012 | Butler et al. |
| 2012/0173269 A1 | 7/2012 | Omidi |
| 2012/0179665 A1 | 7/2012 | Baarman et al. |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1* | 11/2012 | Sandvick ..................... 340/584 |
| 2012/0290051 A1 | 11/2012 | Boyden et al. |
| 2012/0315609 A1 | 12/2012 | Miller-Kovach et al. |
| 2012/0321759 A1 | 12/2012 | Marinkovich et al. |
| 2013/0018761 A1 | 1/2013 | Kwak |
| 2013/0030944 A1 | 1/2013 | Nicod et al. |
| 2013/0033031 A1 | 2/2013 | Key |
| 2013/0035787 A1 | 2/2013 | Canter |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080098 A1 | 3/2013 | Hadad et al. |
| 2013/0080784 A1 | 3/2013 | Oertli |
| 2013/0105470 A1 | 5/2013 | De Luca et al. |
| 2013/0105565 A1 | 5/2013 | Kamprath |
| 2013/0117310 A1 | 5/2013 | Chai et al. |
| 2013/0171305 A1 | 7/2013 | Cescot et al. |
| 2013/0209615 A1 | 8/2013 | Lee et al. |
| 2013/0213951 A1 | 8/2013 | Boedicker et al. |
| 2013/0214938 A1 | 8/2013 | Kim |
| 2013/0231711 A1 | 9/2013 | Kaib |
| 2013/0255507 A1 | 10/2013 | Meunier et al. |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273222 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0287060 A1 | 10/2013 | Langdoc et al. |
| 2013/0290364 A1 | 10/2013 | Minvielle |
| 2013/0295532 A1 | 11/2013 | Minvielle |
| 2013/0297642 A1 | 11/2013 | Minvielle |
| 2013/0302483 A1 | 11/2013 | Riefenstein |
| 2013/0306627 A1 | 11/2013 | Libman et al. |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |
| 2013/0327231 A1 | 12/2013 | Holman et al. |
| 2013/0337516 A1 | 12/2013 | Herrema |
| 2014/0018636 A1 | 1/2014 | Contant et al. |
| 2014/0026762 A1 | 1/2014 | Riefenstein |
| 2014/0037805 A1 | 2/2014 | Minvielle |
| 2014/0038140 A1 | 2/2014 | Minvielle |
| 2014/0041530 A1 | 2/2014 | Luckhardt et al. |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0191025 A1 | 7/2014 | Minvielle |
| 2014/0214714 A1 | 7/2014 | Minvielle |
| 2014/0236359 A1 | 8/2014 | Minvielle |
| 2014/0263640 A1 | 9/2014 | Heit et al. |
| 2014/0279088 A1 | 9/2014 | Hurst et al. |
| 2014/0290395 A1 | 10/2014 | Minvielle |
| 2014/0290396 A1 | 10/2014 | Minvielle |
| 2014/0339296 A1 | 11/2014 | McAdams et al. |
| 2014/0347491 A1 | 11/2014 | Connor |
| 2014/0364971 A1 | 12/2014 | Minvielle |
| 2014/0364972 A1 | 12/2014 | Minvielle |
| 2015/0012122 A1 | 1/2015 | Minvielle |
| 2015/0017252 A1 | 1/2015 | Garland et al. |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100350 A1 | 4/2015 | Minvielle |
| 2015/0100462 A1 | 4/2015 | Minvielle |
| 2015/0118659 A1 | 4/2015 | Meyer |
| 2015/0149120 A1 | 5/2015 | Burkhardt et al. |
| 2015/0227887 A1 | 8/2015 | Minvielle |
| 2015/0235566 A1 | 8/2015 | Minvielle |
| 2015/0236913 A1 | 8/2015 | Nakano et al. |
| 2015/0269867 A1 | 9/2015 | Minvielle |
| 2015/0289324 A1 | 10/2015 | Rober et al. |
| 2015/0320808 A1 | 11/2015 | Burcelin et al. |
| 2015/0366006 A1 | 12/2015 | Ben-Shmuel et al. |
| 2016/0091218 A1 | 3/2016 | Omagari et al. |

(56) References Cited

U.S. PATENT DOCUMENTS

| | | | |
|---|---|---|---|
| 2016/0180739 A1 | 6/2016 | Minvielle | |
| 2016/0217420 A1 | 7/2016 | Minvielle | |
| 2016/0220059 A1 | 8/2016 | Wachtler et al. | |
| 2016/0260352 A1 | 9/2016 | Ortiz | |
| 2016/0342144 A1 | 11/2016 | Minvielle | |
| 2016/0350704 A1 | 12/2016 | Minvielle | |
| 2016/0350715 A1 | 12/2016 | Minvielle | |
| 2017/0011653 A1 | 1/2017 | Minvielle | |
| 2017/0108441 A1 | 4/2017 | Nault et al. | |
| 2017/0208850 A1 | 4/2017 | Minvielle | |
| 2017/0320655 A1 | 11/2017 | Minvielle | |

FOREIGN PATENT DOCUMENTS

| | | |
|---|---|---|
| CN | 102033043 A | 4/2011 |
| DE | 19843016 A1 | 3/2000 |
| DE | 10 2005 040206 A1 | 2/2007 |
| DE | 10 2007 032 303 A1 | 1/2008 |
| EP | 1117055 A2 | 7/2001 |
| EP | 1 172 752 A2 | 1/2002 |
| EP | 1 253 203 A1 | 10/2002 |
| EP | 1 382 912 A1 | 1/2004 |
| EP | 2 388 564 A1 | 11/2011 |
| FR | 2813683 A1 | 3/2002 |
| GB | 2312054 A | 10/1997 |
| JP | 10302105 A | 11/1998 |
| JP | 2002-022177 A | 1/2002 |
| JP | 2002-251518 A | 9/2002 |
| JP | 2002-288359 A | 10/2002 |
| JP | 2002-358591 | 12/2002 |
| JP | 2002-366737 A | 12/2002 |
| JP | 2003-535416 A | 11/2003 |
| JP | 2009-059231 A | 3/2009 |
| JP | 11-045297 A | 3/2011 |
| JP | 5167730 B2 | 3/2013 |
| KR | 2003-0032835 A | 4/2003 |
| KR | 2006-0122596 A | 11/2006 |
| KR | 20100097445 A | 9/2010 |
| WO | 91/13304 A1 | 9/1991 |
| WO | WO 01/93036 A1 | 12/2001 |
| WO | 02/06984 | 1/2002 |
| WO | 02/37375 A1 | 5/2002 |
| WO | WO 2005/104444 A2 | 11/2005 |
| WO | WO 2007/108906 A2 | 9/2007 |
| WO | 2008054231 A1 | 5/2008 |
| WO | 2009/157750 A1 | 12/2009 |
| WO | WO 2013/126579 A1 | 8/2013 |
| WO | WO 2013/134325 A1 | 9/2013 |
| WO | WO 2013/134544 A1 | 9/2013 |
| WO | WO 2013/142218 A1 | 9/2013 |
| WO | WO 2013/158571 A2 | 10/2013 |
| WO | WO 2013/158572 A2 | 10/2013 |
| WO | WO 2013/158576 A1 | 10/2013 |
| WO | WO 2013/176800 A1 | 11/2013 |
| WO | WO 2013/180925 A2 | 12/2013 |
| WO | WO 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | 2015/054082 | 4/2015 |
| WO | WO 2015/069325 A1 | 5/2015 |
| WO | WO 2015/069950 A1 | 5/2015 |
| WO | WO 2015/073569 A1 | 5/2015 |

OTHER PUBLICATIONS

Office Action in U.S. Appl. No. 13/485,866, dated Jul. 26, 2016.
Office Action in U.S. Appl. No. 14/080,768, dated Sep. 8, 2016.
Office Action in U.S. Appl. No. 13/485,854, dated Mar. 17, 2016.
Office Action in U.S. Appl. No. 13/485,883, dated Apr. 19, 2016.
Office Action in U.S. Appl. No. 13/485,916, dated Feb. 18, 2016.
Office Action in U.S. Appl. No. 13/646,632, dated Apr. 21, 2016.
Notice of Allowance in U.S. Appl. No. 13/861,300, dated Apr. 15, 2016.
Office Action in U.S. Appl. No, 13/888,353, dated Apr. 21, 2016.
Office Action in U.S. Appl. No. 13/937,167 dated Mar. 2, 2016.
Office Action in U.S. Appl. No. 14/304,671, dated Apr. 8, 2016.
Office Action in U.S. Appl. No. 14/203,353, dated Mar. 7, 2016.
Office Action in U.S. Appl. No. 14/466,805, dated Mar. 8, 2016.
Office Action in U.S. Appl. No. 14/286,627, dated Mar. 3, 2016.
Office Action in U.S. Appl. No. 14/307,365, dated May 3, 2016.
Office Action in U.S. Appl. No. 14/667,608 dated Mar. 16, 2016.
Office Action in U.S. Appl. No. 14/860,340 dated Apr. 20, 2016.
Qiao, Y, "Routine Techniques for Monitoring the Value of Animal Meals", Unknown, 2001, 224 pgs. https://books.google.com/books/about/Routine_Techniques_for_Monitoring_the_Nu.html?id=LhsktkRPZ7EC.
Wijtzes, T., et al., "A decision support system for the prediction of microbial food safety and food quality", International Journal of Food Microbiology 42 (1997) 79-90.
Search Report and Written Opinion in Singapore application 10201406107X dated Feb. 11, 2016.
Extended European Search Report in European Application No. 13757527.0, dated Mar. 24, 2016.
AlKanhal et al., "Changes in protein nutritional quality in fresh and recombined ultra high temperature treated milk during storage.", Int. J. Food Sci. Nutr., Nov. 2001; 52(6): 509-14, 2 pgs.
Office Action in U.S. Appl. No. 13/485,863, dated Dec. 30, 2015.
Office Action in U.S. Appl. No. 13/485,866, dated Dec. 24, 2015.
Office Action in U.S. Appl. No. 13/485,878, dated Feb. 1, 2016.
Office Action in U.S. Appl. No. 131485,883, dated Oct. 28, 2015.
Office Action in U.S. Appl. No. 13/646,632, dated Dec. 31, 2015.
Office Action in U.S. Appl. No. 13/729,548, dated Feb. 5, 2016.
Office Action in U.S. Appl. No. 13/732,050, dated Jan. 15, 2016.
Office Action in U.S. Appl. No. 13/887,150 dated Nov. 20, 2015.
Office Action in U.S. Appl. No. 13/948,004, dated Dec. 17, 2015,.
Office Action in U.S. Appl. No. 14/080,768, dated Jan. 25, 2016.
Office Action in U.S. Appl. No. 14/260,115, dated Dec. 4, 2015.
Office Action in U.S. Appl. No. 14/466,805, dated Nov. 20, 2015.
Office Action in U.S. Appl. No. 14/466,824, dated Jan. 13, 2016.
Office Action in U.S. Appl. No. 14/467,433, dated Dec. 24, 2015.
Office Action in U.S. Appl. No. 14/667,608 dated Nov. 2, 2015.
Extended European Search Report in European Application No. 13778362.7, dated Nov. 27, 2015.
Extended European Search Report in European Application No. 13777608.4, dated Nov. 19, 2015.
Extended European Search Report in European Application No. 13793073.1 dated Jan. 14, 2016.
Extended European Search Report in European Application No. 13778042.5, dated Nov. 20, 2015.
PCT International Search Report and Written Opinion in International Application No. PCT/US2015/045562, dated Nov. 23, 2015.
Office Action in U.S. Appl. No. 13/485,850 dated Sep. 24, 2015.
Office Action in U.S. Appl. No. 13/485,854, dated Aug. 21, 2015.
Office Action in U.S. Appl. No. 13/485,863, dated Sep. 2, 2015.
Office Action in U.S. Appl. No. 13/485,878, dated Jul. 8, 2015.
Office Action in U.S. Appl. No. 13/485,916, dated Sep. 18, 2015.
Office Action in U.S. Appl. No. 13/646,632, dated Oct. 20, 2015.
Office Action in U.S. Appl. No. 13/684,113, dated Jul. 1, 2015.
Office Action in U.S. Appl. No. 13/729,548, dated Jul. 14, 2015.
Office Action in U.S. Appl. No. 13/732,050, dated Jun. 23, 2015.
Office Action in U.S. Appl. No. 13/771,004, dated Oct. 22, 2015.
Office Action in U.S. Appl. No. 13/861,300 dated Sep. 29, 2015.
Office Action in U.S. Appl. No. 13/888,353, dated Sep. 9, 2015.
Notice of Allowance in U.S. Appl. No. 13/931,733, dated Jun. 11, 2015.
Office Action in U.S. Appl. No. 13/937,167 dated Aug. 17, 2015.
Office Action in U.S. Appl. No. 13/948,071, dated Jul. 20, 2015.
Office Action in U.S. Appl. No. 13/948,078, dated Aug. 5, 2015.
Office Action in U.S. Appl. No. 13/948,004, dated Jul. 31, 2015.
Office Action in U.S. Appl. No. 14/080,768, dated Jun. 17, 2015.
Office Action in U.S. Appl. No. 14/304,671, dated Sep. 3, 2015.
Office Action in U.S. Appl. No. 14/203,353, dated Aug. 20, 2015.
Office Action in U.S. Appl. No. 14/286,627, dated Oct. 9, 2015.
Office Action in U.S. Appl. No. 14/725,114 dated Oct. 22, 2015.

(56) References Cited

OTHER PUBLICATIONS

Further Exam Report in European Application No. 13731655.0, dated Aug. 13, 2015.
Search Report and Written Opinion in Singapore application 2013045448 dated Jun. 24, 2015.
Extended European Search Report in European Application No. 13763782.3, dated Jun. 11, 2015.
PCT International Search Report and Written Opinion in International Application No. PCT/US2015/035872, dated Sep. 3, 2015.
PCT International Search Report and Written Opinion in International Application No. PCT/US2015/035875, dated Sep. 4, 2015.
Office Action in U.S. Appl. No. 13/485,850, dated Mar. 19, 2015.
Office Action in U.S. Appl. No. 13/485,866, dated May 7, 2015.
Office Action in U.S. Appl. No. 13/485,883, dated May 20, 2015.
Office Action in U.S. Appl. No. 13/485,916, dated Mar. 27, 2015.
Office Action in U.S. Appl. No. 13/646,632, dated Mar. 26, 2015.
Office Action in U.S. Appl. No. 13/685,575, dated May 5, 2015.
Office Action in U.S. Appl. No. 13/888,353, dated Mar. 26, 2015.
Notice of Allowance in U.S. Appl. No. 13/921,078, dated Apr. 1, 2015.
Notice of Allowance in U.S. Appl. No. 14/044,851, dated Mar. 31, 2015.
Office Action in U.S. Appl. No. 14/203,353, dated Mar. 31, 2015.
Office Action in U.S. Appl. No. 14/260,115, dated Apr. 16, 2015.
Office Action in U.S. Appl. No. 14/466,805, dated Apr. 13, 2015.
Office Action in U.S. Appl. No. 14/286,627, dated Apr. 24, 2015.
Office Action in U.S. Appl. No. 14/466,824, dated May 7, 2015.
Office Action in U.S. Appl. No. 14/467,433, dated May 8, 2015.
Notice of Allowance in U.S. Appl. No. 14/306,111, dated Mar. 17, 2015.
PCT International Search Report and Written Opinion in International Application No. PCT/US2014/044700, dated May 18, 2015.
Bell, S. et al., "Report on nutrient losses and gains factors used in European food composition databases", Technical Report, Apr. 2006, 66 pages (Retrieved from the Internet on Mar. 2, 2015 at: http://www.eurofir.net).
Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf ).
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Office Action in U.S. Appl. No. 13/485,863, dated Feb. 9, 2015.
Office Action in U.S. Appl. No. 13/485,883, dated Feb. 3, 2015.
Office Action in U.S. Appl. No. 13/485,900, dated Feb. 3, 2015.
Office Action in U.S. Appl. No. 13/684,113, dated Dec. 15, 2014.
Office Action in U.S. Appl. No. 13/771,004, dated Mar. 10, 2015.
Office Action in U.S. Appl. No. 13/861,300 dated Feb. 24, 2015.
Office Action in U.S. Appl. No. 13/931,733, dated Mar. 10, 2015.
Office Action in U.S. Appl. No. 14/044,851, dated Jan. 5, 2015.
Notice of Allowance in U.S. Appl. No. 14/059,441, dated Jan. 5, 2015.
Notice of Allowance in U.S. Appl. No. 14/137,963, dated Jan. 28, 2015.
Office Action in U.S. Appl. No. 14/304,671, dated Feb. 4, 2015.
PCT International Search Report and Written Opinion in International Application No. PCT/US2014/033084, dated Mar. 6, 2015.
PCT International Search Report and Written Opinion in International Application No. PCT/US2014/036570, dated Mar. 10, 2015.
PCT International Search Report and Written Opinion in International Application No. PCT/US2014/045807, dated Jan. 22, 2015.
PCT International Search Report and Written Opinion in International Application No. PCT/US14/59186, dated Dec. 22, 2014.
PCT International Search Report and Written Opinion in International Application No. PCT/US2014/065281, dated Mar. 13, 2015.
PCT International Search Report and Written Opinion in International Application No. PCT/US2014/064434, dated Feb. 20, 2015.
Communication Pursuant to Article 94(3) in European Application No. 13731655.0, dated Jan. 22, 2015.
Extended European Search Report in European Application No. 13751912.0, dated Feb. 25, 2015.
"Automated Fruit Recognition" Fraunhofer, accessed online Nov. 13, 2014 and, available at http://www.iosb.fraunhofer.de/servlet/is/33328/.
Chung, I-C. et al., "A Portable Electrochemical Sensor for Caffeine and (-)Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2008, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.
De Vos, K. et al., "Multiplexed antibody detection with an array of silicon-on-insulator microring resonators", IEEE, Photonics Journal, vol. 1, Issue 4, Oct. 2009, pp. 225-235.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al, "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Focke, M. et al., "Lab-on-a-Foil: microfluidics on thin and flexible films", Lab on a Chip, vol. 10, Issue 11, published online Mar. 19, 2010, pp. 1365-1386.
Gartia, M. et al., "Colorimetric plasmon resonance imaging using nano lycurgus cup arrays", Advanced Optical Materials, vol. 1, Issue 1, Jan. 2013, pp. 68-76.
Huang, et al., "A passive radiofrequency pH sensing tag for wireless food quality monitoring", IEEE Sensors Journal, vol. 12, Issue 3, Mar. 2012, pp. 487-495.
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Preechaburana, et al., "Surface Plasmon Resonance Chemical Sensing on Cell Phones", Angewandte Chemie International Edition, vol. 51, Issue 46, pp. 11585-11588, first published online Oct. 16, 2012.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Scampicchio, M. et al., "Optical nanoprobes based on gold nanoparticles for sugar sensing", Nanotechnology, vol. 20, Issue 13, Apr. 1, 2009, 5 pages.
Zhu, H. et al., "Quantum dot enabled detection of *Escherichia coli* using a cell-phone", Analyst, vol. 137, Issue 11, Jun. 7, 2012, pp. 2541-2544.
Office Action in U.S. Appl. No. 13/485,850, dated Sep. 29, 2014.
Office Action in U.S. Appl. No. 13/485,878, dated Jun. 5, 2014.
Advisory Action in U.S. Appl. No. 13/485,878, dated Sep. 16, 2014.
Office Action in U.S. Appl. No. 13/685,575, dated Oct. 27, 2014.
Office Action in U.S. Appl. No. 13/729,548, dated Dec. 2, 2014.

(56) References Cited

OTHER PUBLICATIONS

Office Action in U.S. Appl. No. 13/888,353, dated May 1, 2014.
Office Action in U.S. Appl. No. 13/888,353, dated Oct. 1, 2014.
Office Action in U.S. Appl. No. 13/921,078, dated Nov. 4, 2014.
Office Action in U.S. Appl. No. 13/931,733, dated Nov. 6, 2014.
Office Action in U.S. Appl. No. 13/937,167, dated Apr. 14, 2014.
Office Action in U.S. Appl. No. 13/948,004, dated Jun. 11, 2014.
Notice of Allowance in U.S. Appl. No. 14/047,817, dated Apr. 14, 2014.
Office Action in U.S. Appl. No. 14/059,441 dated Jul. 10, 2014.
Notice of Allowance in U.S. Appl. No. 14/074,664, dated Jun. 2, 2014.
Office Action in U.S. Appl. No. 14/137,963, dated Aug. 5, 2014.
Office Action in U.S. Appl. No. 14/306,111, dated Nov. 13, 2014.
Office Action in U.S. Appl. No. 29/497,888, dated Nov. 19, 2014.
PCT International Search Report and Written Opinion in International Application No. PCT/US2014/044696, dated Oct. 10, 2014.
PCT International Search Report and Written Opinion in International Application No. PCT/US2014/045796, dated Oct. 15, 2014.
PCT International Search Report and Written Opinion in International Application No. PCT/US2014/045798, dated Oct. 15, 2014.
European Examination Report in European Application No. 13757669.0, dated Oct. 13, 2014.
Ghasemi-Varnamkhasti, M. et al., "Biomimetic-based odor and taste sensing systems to food quality and safety characterization: An overview on basic principles and recent achievements", Journal of Food Engineering, vol. 100, pp. 377-387, May 2010.
Statement in accordance with the Notice from the European Patent Office, dated Oct. 1, 2007, concerning business methods.
Notice from the European Patent Office, dated Oct. 1, 2007, concerning business methods, Official Journal EPO, pp. 592-593.
Office Action in U.S. Appl. No. 13/485,850, dated Mar. 20, 2014.
Office Action in U.S. Appl. No. 13/771,004, dated Apr. 4, 2014.
Office Action in U.S. Appl. No. 14/059,441, dated Feb. 11, 2014.
Office Action in U.S. Appl. No. 13/732,050, dated Apr. 10, 2014.
Extended European Search Report in European Application No. 13757669.0, dated Jan. 31, 2014.
Extended European Search Report in European Application No. 13731655.0, dated Feb. 24, 2014.
Notice of Allowance in U.S. Appl. No. 13/931,744, dated Feb. 28, 2014.
Office Action in U.S. Appl. No, 13/485,850, dated Sep. 30, 2013.
Office Action in U.S. Appl. No. 13/485,878, dated Oct. 24, 2013.
Office Action in U.S. Appl. No. 13/685,575, dated Oct. 24, 2013.
Office Action in U.S. Appl. No. 13/732,050, dated Oct. 24, 2013.
Office Action in U.S. Appl. No, 13/771,004, dated Jul. 8, 2013.
Office Action in U.S. Appl. No. 13/888,353, dated Jul. 25, 2013 (restriction).
Office Action in U.S. Appl. No. 13/888,353, dated Dec. 4, 2013 (restriction).
Office Action in U.S. Appl. No. 13/900,426, dated Aug. 8, 2013.
Office Action in U.S. Appl. No. 13/931,744, dated Aug. 20, 2013.
Office Action in U.S. Appl. No. 13/937,167, dated Oct. 28, 2013.
Office Action in U.S. Appl. No. 13/948,004, dated Oct. 24, 2013.
Office Action in U.S. Appl. No. 14/047,817, dated Nov. 29, 2013.
Office Action in U.S. Appl. No. 14/059,441, dated Dec. 20, 2013.
Office Action in U.S. Appl. No. 14/074,664, dated Jan. 8, 2014.
Notice of Allowance in U.S. Appl. No. 13/900,426, dated Dec. 16, 2013.
PCT International Search Report and Written Opinion in International Application No. PCT/US13/36666, dated Oct. 4, 2013.
PCT International Search Report and Written Opinion in International Application No. PCT/US2013/036668, dated Dec. 6, 2013.
PCT International Search Report and Written Opinion in International Application No. PCT/US2013/036670, dated Aug. 19, 2013.
PCT International Search Report and Written Opinion in International Application No. PCT/US2013/036673, dated Aug. 20, 2013.
PCT International Search Report and Written Opinion in International Application No. PCDUS2013/040445, dated Oct. 25, 2013.
Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Greenfield, H. et al., "Food composition data," FAO, 2003 ("FAO").
Montesinos, F., "Plant-associated Microorganisms: a View from the Scope of Microbiology", International Microbiology, Dec. 2003, vol. 6, Issue 4, pp. 221-223.
Sinclair, D.A. et al., "Unlocking the Secrets of Longevity Genes", Scientific American, Mar. 2006, vol. 294, Issue 3, pp. 48-57.
Diller, K.R., "Stress Protein Expression Kinetics", Annual Review of Biomedical Engineering, 2006, vol. 8, pp. 403-424.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Ni, Fu-Tai et al., "Gene Expression and Regulation of Higher Plants Under Soil Water Stress", Current Genomics, Jun. 2009, vol. 10, pp. 269-280.
Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Kingsmore, S.F., "Multiplexed Protein Measurement: Technologies and Applications of Protein and Antibody Arrays", Nature Reviews Drug Discovery, Apr. 2006, vol. 5, pp. 310-321.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Perks, B., "Fighting Food Fraud with Science", Text Reproduced from Chemistry World, 2007, vol. 4 (9), pp. 48-52.
Montealegre, C. et al., "Traceability Markers to the Botanical Origin in Olive Oils", Journal of Agricultural and Food Chemistry, 2010, vol. 58 (1), pp. 28-38.
Martins-Lopes, P. et al., "DNA Markers for Portuguese Olive Oil Fingerprinting", Journal of Agricultural and Food Chemistry, 2008, vol. 56 (24), pp. 11786-11791.
Garcia-Gonzalez, D.L. et al., "Research in Olive Oil: Challenges for the Near Future", Journal of Agricultural and Food Chemistry, 2010, vol. 58 (24), pp. 12569-12577.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., " Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Rashidi, L. et al., "The Applications of Nanotechnology in Food Industry", Critical Reviews in Food Science and Nutrition, 2011, vol. 51, Issue 8, pp. 723-730.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Chaudhry, Q.et al., "Applications and Implications of Nanotechnologies for the Food Sector", Food Additives and Contaminants: Part a, Mar. 2008, vol. 25, Issue 3, pp. 241-258.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Walt, D.R., "Electronic Noses: Wake Up and Smell the Coffee", Analytical Chemistry, Feb. 1, 2005, vol. 77 (3), p. A-45.

(56) References Cited

OTHER PUBLICATIONS

Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Rock, F. et al., "Electronic Nose: Current Status and Future Trends", Chemical Reviews, 2008, vol. 108, No. 2, pp. 705-725.
Hierlemann, A. et al., "Higher-Order Chemical Sensing", Chemical Reviews, 2008, vol. 108, No. 2, pp. 563-613.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
Grate, J.W., "Acoustic Wave Microsensor Arrays for Vapor Sensing", Chemical Reviews, 2000, vol. 100, No. 7, pp. 2627-2647.
Janata, J. et al., "Conducting Polymers in Electronic Chemical Sensors", Nature Materials, Jan. 2003, vol. 2, pp. 19-24.
Wolfbeis, 0.5., "Materials for Fluorescence-based Optical Chemical Sensors", Journal of Materials Chemistry, 2005, vol. 15, pp. 2657-2669.
James, D. et al., "Chemical Sensors for Electronic Nose Systems", Microchimica Acta, Feb. 2005, vol. 149, pp. 1-17.
Primrose, S. et al., "Food Forensics: Methods for Determining the Authenticity of Foodstuffs", Trends in Food Science & Technology, Dec. 2010, vol. 21 (12), pp. 582-590.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
U.S. Office Action in U.S. Appl. No. 13/485,850 dated May 9, 2013.
U.S. Office Action in U.S. Appl. No. 13/560,965 dated Feb. 1, 2013.
U.S. Office Action in U.S. Appl. No. 13/685,575 dated May 6, 2013.
U.S. Office Action in U.S. Appl. No. 13/750,804 dated Mar. 12, 2013.
U.S. Office Action in U.S. Appl. No. 13/771,004 dated May 15, 2013.
Notice of Allowance in U.S. Appl. No. 13/560,965 dated Mar. 22, 2013.
Notice of Allowance in U.S. Appl. No. 13/750,804 dated May 31, 2013.
PCT International Search Report and Written Opinion in International Application No. PCT/US2013/029686, dated May 13, 2013.
PCT International Search Report and Written Opinion in International Application No. PCT/US2013/031106, dated May 31, 2013.
PCT International Search Report and Written Opinion in International Application No. PCT/US13/27148, dated Jun. 18, 2013.
PCT International Search Report and Written Opinion in International Application No. PCT/US13/29219, dated Jun. 20, 2013.
Thakur, M. et al., "Food Traceability, R&D Norway" Food Technology, Apr. 2012, p. 42-46.
Hoffman, B., "IBM Announces Food Traceability Technology," Food+Tech Connect, Oct. 19, 2011, 2 pages.
"SIRA Technologies Food Sentinel System Thermal Barcode for Packaging," Sustainable is Good: Lifestyle and Design blog, Mar. 4, 2009, 2 pages.
Office Action in U.S. Appl. No. 13/485,866, dated Aug. 3, 2017.
Office Action in U.S. Appl. No. 13/602,040, dated Oct. 23, 2013.
Office Action in U.S. Appl. No. 13/602,040, dated Jul. 17, 2014.
Office Action in U.S. Appl. No. 13/602,040, dated Jul. 6, 2015.
Office Action in U.S. Appl. No. 13/602,040, dated May 6, 2016.
Notice of Allowance in U.S. Appl. No. 13/602,040 dated Nov. 30, 2016.
Office Action in U.S. Appl. No. 13/646,632, dated Jan. 10, 2017.
Office Action in U.S. Appl. No. 13/646,632, dated Aug. 23, 2017.
Office Action in U.S. Appl. No. 13/685,575, dated Jan. 18, 2017.
Office Action in U.S. Appl. No. 13/685,575, dated Aug. 14, 2017.
Office Action in U.S. Appl. No. 13/684,113, dated Feb. 1, 2017.
Office Action in U.S. Appl. No. 13/948,004, dated Feb. 13, 2017.
Office Action in U.S. Appl. No. 14/080,768, dated Apr. 13, 2017.
Office Action in U.S. Appl. No. 14/080,768, dated Jul. 6, 2017.
Office Action in U.S. Appl. No. 14/520,267 dated Nov. 21, 2016.
Office Action in U.S. Appl. No. 14/860,340 dated Sep. 9, 2016.
Office Action in U.S. Appl. No. 15/226,866 dated May 11, 2017.
Office Action in U.S. Appl. No. 15/226,866 dated Aug. 30, 2017.
Notice of Allowance in U.S. Appl. No. 15/241,019 dated Apr. 5, 2017.
Office Action in U.S. Appl. No. 15/276,736 dated May 9, 2017.
France Preliminary Search Report and Written Opinion in 1453167 dated Feb. 24, 2017.
Notice for Reasons of Rejection in Japanese Application No. 2014-558826 dated Mar. 17, 2017.
Notice for Reasons of Rejection in Japanese Application No. 2015-507092 dated May 8, 2017.
Notice for Reasons of Rejection in Japanese Application No. 2015-507092 dated Aug. 21, 2017.
Extended European Search Report in European Application No. 14783369.3, dated Jan. 5, 2017.
Extended European Search Report in European Application No. 14816751.3, dated Oct. 31, 2016.
Korean Notice of Non-Final Rejection Application No. 10-2016-7002508 dated Jul. 20, 2017.
European Search Report in European Application No. 14860809.4, dated May 22, 2017.
Extended European Search Report in European Application No. 14862157.6, dated May 8, 2017.
PCT International Search Report and Written Opinion in International Application No. PCT/US2017/043520, dated Aug. 11, 2017.
Arora, P. et al., "An overview of transducers as platform for the rapid detection of foodborne pathogens", Appl. Microbial. Biotechnol., vol. 97, Issue 5, pp. 1829-1840, Jan. 18, 2013 (Published online).
Kameoka, T., "Application of Color Information to the Fruit Cultivation", Japanese Journal of Optics, The Optical Society of Japan, Nov. 2002, vol. 31, No. 11, pp. 813.
Nakata, Eriko; Research regarding usefulness of a freshness evaluation system and a biothermometer as an accumulated thermometer, Collection of summaries of lectures of Japan Society for Food Engineering 9th (fiscal year 2008) Annual Meeting, Jul. 17, 2008, p. 95.
Overseas Note, The Food Industry, Kourin corporation, Apr. 30, 1993; vol. 36, No. 10, p. 13.
Office Action in U.S. Appl. No. 14/730,005 dated Sep. 21, 2017.
Office Action in U.S. Appl. No. 14/702,573 dated Sep. 22, 2017.
Notice of Allowance in U.S. Appl. No. 13/684,113, dated Oct. 30, 2017.
Notice of Allowance in U.S. Appl. No. 15/276,736 dated Nov. 8, 2017.
Office Action in U.S. Appl. No. 14/725,114 dated Nov. 20, 2017.
PCT International Search Report and Written Opinion in International Application No. PCT/US2017/034085, dated Oct. 12, 2017.

\* cited by examiner

CONDITIONING SYSTEM FOR NUTRITIONAL SUBSTANCES

RELATED PATENT APPLICATIONS

This application is a divisional of U.S. patent application Ser. No. 13/602,040, filed Aug. 31, 2012, now U.S. Pat. No. 9,619,781, which is a continuation of U.S. patent application Ser. No. 13/485,866, filed May 31, 2012, which claims priority to U.S. Provisional Application No. 61/624,745, filed Apr. 16, 2012, U.S. Provisional Application No. 61/624,765, filed Apr. 16, 2012, and U.S. Provisional Application No. 61/624,788, filed Apr. 16, 2012, each of which is hereby incorporated by reference herein in its entirety.

FIELD OF THE INVENTION

The present inventions relate to condition systems for preparation of nutritional substances using information regarding source, preservation and current information, prior transformation information, consumer preference information, including recipe information to control one or more conditioning systems.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. One reason is the nutritional substance industries have tended to act like "silo" industries. Each group in the food and beverage industry: growers, packagers, processors, distributors, retailers, and preparers work separately, and either shares no information, or very little information, between themselves. There is generally no consumer access to, and little traceability of, information regarding the creation and/or origin, preservation, processing, preparation, or consumption of nutritional substances. It would be desirable for such information be available to the consumers of nutritional substances, as well as all participants in the food and beverage industry—the nutritional substance supply system.

While the nutritional substance supply system has endeavored over the last 50 years to increase the caloric and ingredients content of nutritional substances produced (which has help reduce starvation in developing countries, but has led to obesity and other problems in developed countries), maintaining, or increasing, the nutritional content of nutritional substances has not been a priority and is done in a synthetic manner. Caloric content refers to the energy in nutritional substances, commonly measured in calories. The caloric content could be represented as sugars and/or carbohydrates in the nutritional substances. The nutritional content, also referred to herein as nutritional value, of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances.

While there has recently been greater attention by consumer organizations, health organizations and the public to the nutritional content of foods and beverages, the food and beverage industry has been slow in responding to this attention. One reason for this may be that since the food and beverage industry operates as silos of those who create nutritional substances, those who preserve and transport nutritional substances, those who transform nutritional substances, and those who finally prepare the nutritional substances for consumption by the consumer, there has been no system wide coordination of management of nutritional content. While each of these silo industries may be able to maintain or increase the nutritional content of the foods and beverages they handle, each silo industry has only limited information and control of the nutritional substances they receive, and the nutritional substances they pass along.

As consumers better understand their need for nutritional substances with higher nutritional content, they will start demanding that the food and beverage industry offer products which include higher nutritional content, and/or at least information regarding nutritional content of such products. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need, not only within each food and beverage industry silo to maintain or improve the nutritional content of their products, but an industry-wide solution to allow the management of nutritional content across the entire cycle from creation to consumption. In order to manage the nutritional content of nutritional substances across the entire cycle from creation to consumption, the nutritional substance industry will need to identify, track, measure, estimate, preserve, transform, condition, and record nutritional content for nutritional substances. Of particular importance is the measurement, estimation, and tracking of changes to the nutritional content of a nutritional substance from creation to consumption. This information could be used, not only by the consumer in selecting particular nutritional substances to consume, but could be used by the other food and beverage industry silos, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be particular nutritional, organoleptic, or aesthetic values, and if changes to those values are perceived as desirable. For example, if a desirable value has been maintained, improved, or minimally degraded, it could be marketed as a premium product.

For example, the grower of sweet corn generally only provides basic information as the variety and grade of its corn to the packager, who preserves and ships the corn to a producer for use in a ready-to-eat dinner. The packager may only tell the producer that the corn has been frozen as loose kernels of sweet corn. The producer may only provide the consumer with rudimentary instructions how to cook or reheat the ready-to-eat dinner in a microwave oven, toaster oven or conventional oven, and only tell the consumer that the dinner contains whole kernel corn among the various items in the dinner. Finally, the consumer of the dinner will likely keep her opinions on the quality of the dinner to herself, unless it was an especially bad experience, where she might contact the producer's customer support program to complain. Very minimal, or no, information on the nutritional content of the ready-to-eat dinner is passed along to the consumer. The consumer knows essentially nothing about changes (generally a degradation, but could be a maintenance or even an improvement) to the nutritional content of the sweet corn from creation, processing, packaging, cooking, preservation, preparation by consumer, and finally consumption by the consumer.

Consumers' needs are changing as consumers are demanding healthier foods, such as "organic foods." Customers are also asking for more information about the nutritional substances they consume, such as specific characteristics' relating not only to nutritional content, but to allergens or digestive intolerances. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state and aesthetic condition of the product after it has been reheated or cooked by the consumer, cannot predict changes to these properties, and cannot inform a consumer of this information to enable the consumer to better meet their needs. For example, the consumer may want to know what proportion of desired organoleptic properties or values, desired nutritional content or values, or desired aesthetic properties or values of the corn in the ready-to-eat dinner remain after cooking or reheating, and the change in the desired nutritional content or values, the desired organoleptic properties or values, or the desired aesthetic properties or values (usually a degradation, but could be a maintenance or even improvement). There is a need to preserve, measure, estimate, store and/or transmit information regarding such nutritional, organoleptic, and aesthetic values, including changes to these values, throughout the nutritional substance supply system. Given the opportunity and a system capable of receiving and processing real time consumer feedback and updates regarding changes in the nutritional, organoleptic, and/or aesthetic value of nutritional substances, consumers can even play a role in updating dynamic information about the nutritional substances they have purchased and/or prepared for consumption, such that that information is available and useful to others in the nutritional substance supply system.

The caloric and nutritional content information for a prepared food that is provided to the consumer is often minimal. For example, when sugar is listed in the ingredient list, the consumer generally does receive any information about the source of the sugar, which can come from a variety of plants, such as sugarcane, beets, or corn, which will affect its nutritional content. Conversely, some nutritional information that is provided to consumers is so detailed, the consumer can do little with it. For example, this this of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, 211 mg 53%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2, 1 g, Polysaturated Fat 3.6 g, Omega 3 fatty acids 108 g, Omega 6 fatty acids 3481, Ash 2.0 g and Water 17.2 g. (%=Daily Value). There is a need to provide information about nutritional substances in a meaningful manner. Such information needs to be presented in a manner that meets the specific needs of a particular consumer. For example, consumers with a medical condition, such as diabetes, would want to track specific information regarding nutritional values associated with sugar and other nutrients in the foods and beverages they consume, and would benefit further from knowing changes in these values or having tools to quickly indicate or estimate these changes in a retrospective, current, or prospective fashion, and even tools to report these changes, or impressions of these changes, in a real-time fashion.

In fact, each silo in the food and beverage industry already creates and tracks some information, including caloric and nutritional information, about their product internally. For example, the famer who grew the corn knows the variety of the seed, condition of the soil, the source of the water, the fertilizers and pesticides used, and can measure the caloric and nutritional content at creation. The packager of the corn knows when it was picked, how it was transported to the packaging plant, how the corn was preserved and packaged before being sent to the ready-to-eat dinner producer, when it was delivered to the producer, and what degradation to caloric and nutritional content has occurred. The producer knows the source of each element of the ready-to-eat dinner, how it was processed, including the recipe followed, and how it was preserved and packaged for the consumer. Not only does such a producer know what degradation to caloric and nutritional content occurred, the producer can modify its processing and post-processing preservation to minimally affect nutritional content. The preparation of the nutritional substance for consumption can also degrade the nutritional content of nutritional substances. Finally, the consumer knows how she prepared the dinner, what condiments were added, and whether she did or did not enjoy it.

If there was a mechanism to share this information, the quality of the nutritional substances, including caloric and nutritional, organoleptic, and aesthetic value, could be preserved and improved. Consumers could be better informed about nutritional substances they select and consume, including the state, and changes in the state, of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality (including nutritional content) information, and historical environmental information could substantially reduce such waste. Collecting, preserving, measuring and/or tracking information about a nutritional substance in the nutritional substance supply system, would allow needed accountability. There would be nothing to hide.

As consumers are demanding more information about what they consume, they are asking for products that have higher and better nutritional content and more closely match good nutritional requirements, and would like nutritional products to actually meet their specific nutritional requirements. While grocery stores, restaurants, and all those who process and sell food and beverages may obtain some information from current nutritional substance tracking systems, such as labels, these current systems can provide only limited information.

Consumers of nutritional substances are sometimes given options on how to prepare nutritional substances they have obtained from the store, such as different cooking devices: microwave ovens, conventional ovens, etc., and/or limited taste preferences such as crunchy or soft. However, if the consumer desires to prepare a specific recipe, they must obtain all the proper ingredients themselves, as well as prepare the recipe themselves including which cooking appliances need to be used. Further, the consumer has no way of knowing the history or current condition of the nutritional substances they obtain for preparing a desired recipe. Still further, the consumer has no way of knowing how to change or modify the conditioning process to achieve desired nutritional, organoleptic, and aesthetic properties after preparation.

An important issue in the creation, preservation, transformation, conditioning, and consumption of nutritional substances are the changes that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional value (often through the use of additives or preservatives), and/or attempts to hide this loss of nutritional value from consumers.

Overall, the examples herein of some prior or related systems and their associated limitations are intended to be illustrative and not exclusive. Other limitations of existing or prior systems will become apparent to those of skill in the art upon reading the following Detailed Description.

OBJECTS OF THE INVENTION

It is an object of the present invention to obtain information regarding the source, packaging and transformation of the nutritional substance to provide to the consumer.

It is another object of the present invention to obtain information regarding the source, packaging and transformation of the nutritional substance, and the conditioning of the nutritional substance to provide to the consumer.

It is a further object of the present invention to modify the conditioning of the nutritional substance according to the source, packaging and/or transformation information.

It is a further object of the present invention to use source, packaging and transformation information to appropriately select the conditioning settings for a single conditioning apparatus and/or multiple conditioning apparatuses.

It is a further object of the present invention to select the conditioning settings according to the preferences and/or needs of the consumer.

It is a further object of the present invention to use external recipe information to modify the conditioning of a nutritional substance according to the needs and/or tastes of the consumer.

It is an object of the present invention to minimize and/or track degradation of nutritional, organoleptic, and/or aesthetic value of nutritional substances, and/or collect, store, and/or transmit information regarding this degradation, through and including the preparation and consumption of the nutritional substances.

It is a further object of the present invention to estimate a change in a nutritional, organoleptic, or aesthetic value of a nutritional substance to be conditioned prior to conditioning.

It is a further object of the present invention to estimate a change in a nutritional, organoleptic, or aesthetic value of a nutritional substance to be conditioned prior to conditioning and to modify the conditioning of the nutritional substance to optimize a desired nutritional, organoleptic, or aesthetic value of the conditioned nutritional substance.

It is a further object of the present invention to estimate a change in a nutritional, organoleptic, or aesthetic value of a nutritional substance to be conditioned prior to conditioning and to modify the conditioning of the nutritional substance to minimize degradation, preserve, or improve a desired nutritional, organoleptic, or aesthetic value of the conditioned nutritional substance, and/or to optimize a specific nutritional, organoleptic, or aesthetic value of the conditioned nutritional substance such that the conditioned nutritional substance meets the consumer's needs and/or preferences.

It is a further object of the present invention to estimate a change in a nutritional, organoleptic, or aesthetic value of a nutritional substance to being conditioned prior to conditioning and communicate the estimated change to a consumer before and/or after conditioning.

It is a further object of the present invention to receive, and reflect through reporting or modification of a nutritional substance database, consumer reports regarding observed or measured changes in nutritional, organoleptic, and/or aesthetic values of nutritional substances they have purchased, are going to prepare, or are going to consume.

SUMMARY OF THE INVENTION

In an embodiment of the present invention, information related to or determined from source, packaging and transformation information of a nutritional substance, and/or component nutritional substances thereof, is transmitted to the consumer prior to and/or following the conditioning of the nutritional substance.

In another embodiment of the present invention, information related to or determined from source, packaging and transformation information of a nutritional substance, and/or component nutritional substances thereof, is used in the conditioning of the nutritional substance to optimize desirable nutritional, organoleptic, or aesthetic values and/or improve a perceived quality of the conditioned nutritional substance.

In another embodiment of the present invention, information related to or determined from source, packaging and transformation information of a nutritional substance, and/or component nutritional substances thereof, is used in the conditioning of the nutritional substance to minimize degradation, preserve, or improve desirable nutritional, organoleptic, or aesthetic values of the conditioned nutritional substance.

In an embodiment of the present invention, information regarding changes in nutritional, organoleptic, or aesthetic properties of a nutritional substance and/or component nutritional substances thereof, resulting from a proposed conditioning of a nutritional substance is transmitted to the consumer before and/or following the conditioning of the nutritional sub stance.

In a further embodiment of the present invention, one or more conditioning apparatuses use information related to, or determined from, source, packaging and/or transformation information of a nutritional substance and/or component nutritional substances thereof, to modify the conditioning of the nutritional substance.

In another embodiment of the present invention, information about the consumer's needs and/or preferences are used by the conditioning apparatus in the preparation of the nutritional substance.

In a further embodiment of the present invention, external recipe information is used by the conditioning apparatus to modify the conditioning of the nutritional substance.

In another embodiment of the present invention information regarding a change of nutritional, organoleptic, and/or aesthetic value of a nutritional substance and/or component nutritional substances thereof, collectively and individually referred to herein as ΔN, is: measured or collected or calculated or created or estimated or indicated or determined in any suitable manner; stored and/or tracked and/or transmitted and/or processed prior to conditioning and/or following conditioning and/or prior to consumption and/or after consumption, such that the degradation of specific nutritional, organoleptic, and/or aesthetic values can be minimized and specific residual nutritional, organoleptic, and/or aesthetic value can be optimized. A change of nutritional, organoleptic, and/or aesthetic value may not occur, in which case ΔN would be zero. The change of nutritional, organoleptic, and/or aesthetic value may be a degradation, in which case ΔN would be negative. The change of nutritional, organoleptic, and/or aesthetic value may be an improvement, in which case ΔN would be positive.

An embodiment of the present invention provides a system for the creation, collection, storage, transmission, and/or processing of information regarding nutritional substances so as to improve, maintain, or minimize degradation of nutritional, organoleptic, and/or aesthetic value of nutritional substances. Additionally, the present invention provides such information for use by the creators, preservers, transformers, conditioners, and consumers of nutritional substances. The nutritional information creation, preservation, and transmission system of the present invention should allow the nutritional substance supply system to improve its ability to minimize degradation of nutritional, organoleptic and/or aesthetic value of the nutritional substance, and/or inform the consumer, creator, packager, transformer, or conditioner about such degradation, or ΔN. While the ultimate goal of the nutritional substance supply system is to minimize degradation of nutritional, organoleptic and/or aesthetic values, or as it relates to ΔN, minimize the negative magnitude of ΔN. However, an interim goal should be providing consumers with significant information regarding any change, particularly degradation, of nutritional, organoleptic and/or aesthetic values of nutritional, and/or component nutritional substances thereof, consumers select and consume, the ΔN, such that desired information regarding specific residual nutritional, organoleptic, and/or aesthetic values can be ascertained using the ΔN. Entities within the nutritional substance supply system who provide such ΔN information regarding nutritional substances, particularly regarding degradation, will be able to differentiate their products from those who obscure and/or hide such information. Additionally, such entities should be able to charge a premium for products which either maintain their nutritional, organoleptic, and/or aesthetic value, or supply more complete information about changes in their nutritional, organoleptic, and/or aesthetic value, the ΔN. Further, entities that supply conditioning equipment and other devices enabling consumer access and utilization of ΔN information will be able to differentiate their products from those that do not enable the consumer to access and utilize ΔN information. Such conditioning equipment will allow consumers to minimize degradation of, preserve, or improve the nutritional, organoleptic, and/or aesthetic value of the nutritional substances they consume. Such conditioners will further enable the consumer to optimize the nutritional, organoleptic, and/or aesthetic value of the nutritional substances they condition and consume according to their individual needs and/or desires.

In an embodiment of the present invention, observed or measured ΔN information can also be provided by consumers, so that it can be received and reflected through reporting or modification of a nutritional substance database, consumer reports regarding observed or measured changes in nutritional, organoleptic, and/or aesthetic values of nutritional substances they have purchased, are going to prepare, or are going to consume.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
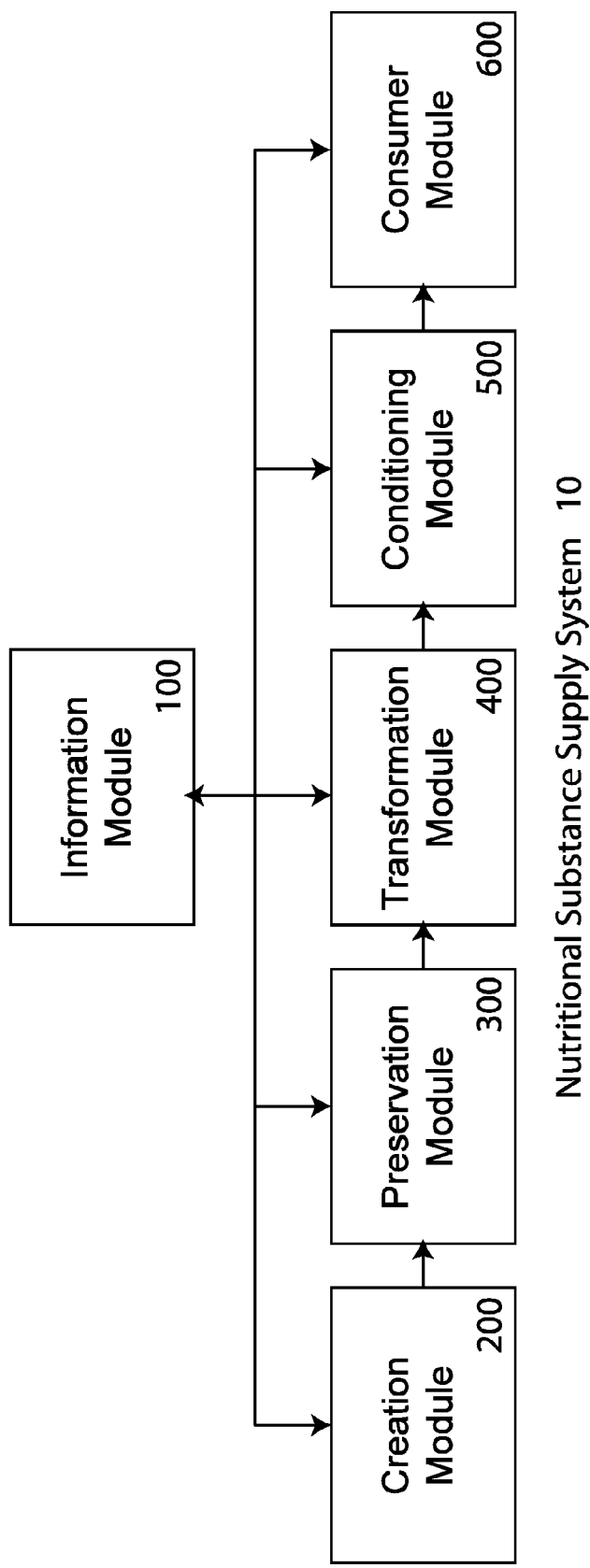
FIG. 1 shows a schematic functional block diagram of a nutritional substance supply relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or prepro-grammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage ecosystem for human consumption, but could also be the feed industry for animal consumption, such as the pet food industry. A goal of the present invention for nutritional substance industry 10 is to create, preserve, transform and trace the change in nutritional, organoleptic and/or aesthetic values of nutritional substances, collectively and individually also referred to herein as $\Delta N$, through their creation, preservation, transformation, conditioning and consumption. While the nutritional substance industry 10 can be composed of many companies or businesses, it can also be integrated into combinations of business serving many roles, or can be one business or even individual. Since $\Delta N$ is a measure of the change in a value of a nutritional substance, knowledge of a prior value (or state) of a nutritional substance and the $\Delta N$ value will provide knowledge of the changed value (or state) of a nutritional substance, and can further provide the ability to estimate a change in value (or state).

Module 200 is the creation module. This can be a system, organization, or individual which creates and/or originates nutritional substances. Examples of this module include a farm which grows produce; a ranch which raises beef; an aquaculture farm for growing shrimp; a factory that synthesizes nutritional compounds; a collector of wild truffles; or a deep sea crab trawler.

Preservation module 300 is a preservation system for preserving and protecting the nutritional substances created by creation module 200. Once the nutritional substance has been created, generally, it will need to be packaged in some manner for its transition to other modules in the nutritional substances industry 10. While preservation module 300 is shown in a particular position in the nutritional substance industry 10, following the creation module 200, it should be understood that the preservation module 300 actually can be placed anywhere nutritional substances need to be preserved during their transition from creation to consumption.

Transformation module 400 is a nutritional substance processing system, such as a manufacturer who processes raw materials such as grains into breakfast cereals. Transformation module 400 could also be a ready-to-eat dinner manufacturer who receives the components, or ingredients, also referred to herein as component nutritional substances, for a ready-to-eat dinner from preservation module 300 and prepares them into a frozen dinner. While transformation module 400 is depicted as one module, it will be understood that nutritional substances may be transformed by a number of transformation modules 400 on their path to consumption.

Conditioning module 500 is a consumer preparation system for preparing the nutritional substance immediately before consumption by the consumer. Conditioning module 500 can be a microwave oven, a blender, a toaster, a convection oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow.

Information module 100 receives and transmits information regarding a nutritional substance between each of the modules in the nutritional substance industry 10 including, the creation module 200, the preservation module 300, the transformation module 400, the conditioning module 500, and the consumer module 600. The nutritional substance information module 100 can be an interconnecting information transmission system which allows the transmission of information between various modules. Information module 100 contains a database, also referred to herein as a dynamic nutritional value database, where the information regarding the nutritional substance resides. Information module 100 can be connected to the other modules by a variety of communication systems, such as paper, computer networks, the internet and telecommunication systems, such as wireless telecommunication systems. In a system capable of receiving and processing real time consumer feedback and updates regarding changes in the nutritional, organoleptic, and/or aesthetic value of nutritional substances, or ΔN, consumers can even play a role in updating a dynamic nutritional value database with observed or measured information about the nutritional substances they have purchased and/or prepared for consumption, so that the information is available and useful to others in the nutritional substance supply system, such as through reports reflecting the consumer input or through modification of ΔN.

Figure 2:
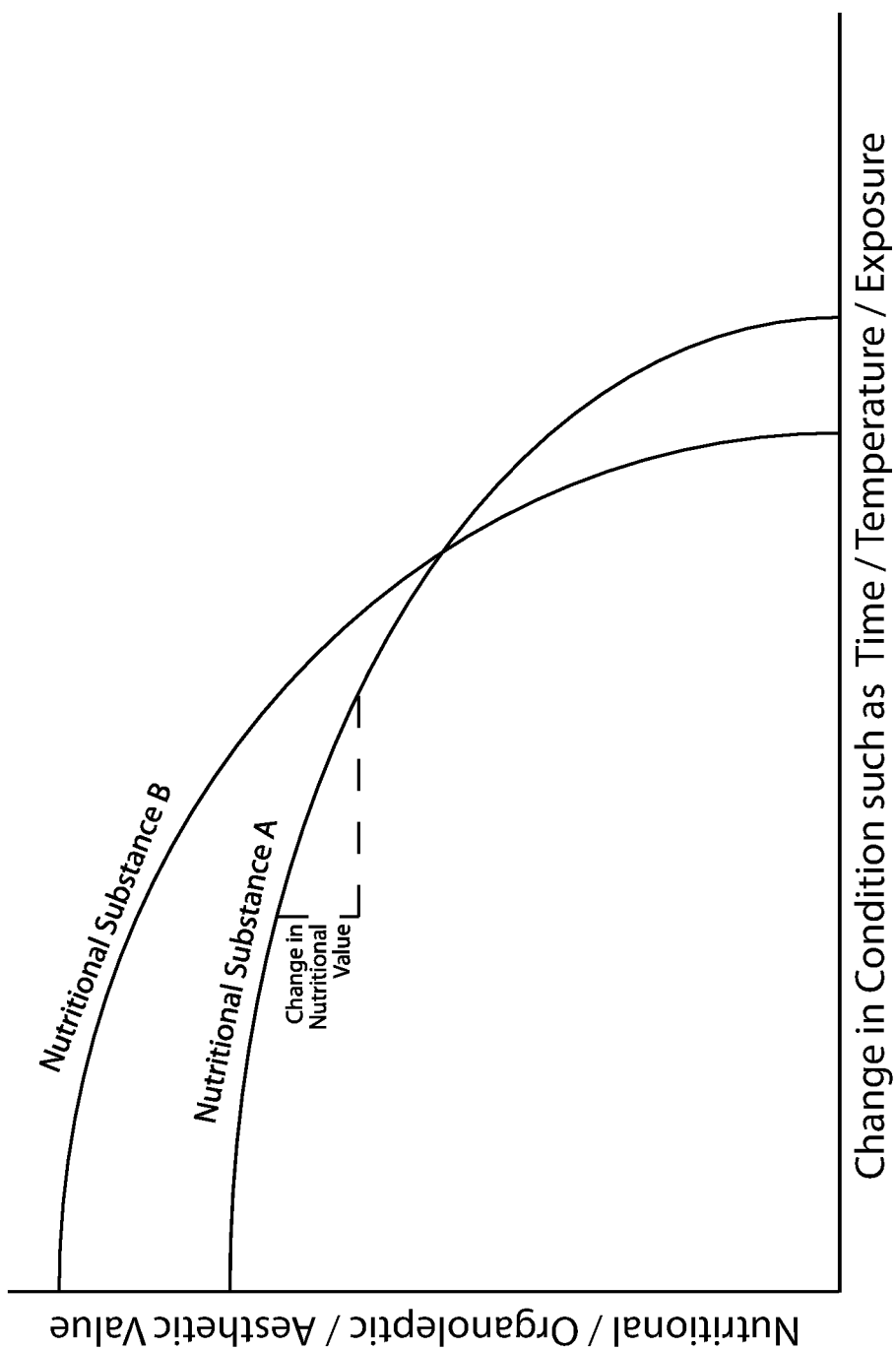
FIG. 2 shows a graph representing a value of a nutritional substance which changes according to a change of condition for the nutritional substance.

FIG. 2 is a graph showing the function of how a nutritional, organoleptic, or aesthetic value of a nutritional substance varies over the change in a condition of the nutritional substance. Plotted on the vertical axis of this graph can be either the nutritional value, organoleptic value, or even the aesthetic value of a nutritional substance. Plotted on the horizontal axis can be the change in condition of the nutritional substance over a variable such as time, temperature, location, and/or exposure to environmental conditions. This exposure to environmental conditions can include: exposure to air, including the air pressure and partial pressures of oxygen, carbon dioxide, water, or ozone; airborne chemicals, pollutants, allergens, dust, smoke, carcinogens, radioactive isotopes, or combustion byproducts; exposure to moisture; exposure to energy such as mechanical impact, mechanical vibration, irradiation, heat, or sunlight; or exposure to materials such as packaging. The function plotted as nutritional substance A could show a ΔN for milk, such as. the degradation of a nutritional value of milk over time. Any point on this curve can be compared to another point to measure and/or describe the change in nutritional value, or the ΔN of nutritional substance A. The plot of the degradation in the same nutritional value of nutritional substance B, also milk, describes the change in nutritional value, or the ΔN of nutritional substance B, a nutritional substance which starts out with a higher nutritional value than nutritional substance A, but degrades over time more quickly than nutritional substance A.

If, in this example, where nutritional substance A and nutritional substance B are milk, this ΔN information regarding the nutritional substance degradation profile of each milk could be used by the consumer in the selection and/or consumption of the milk. If the consumer has this information at time zero when selecting a milk product for purchase, the consumer could consider when the consumer plans to consume the milk, whether that is on one occasion or multiple occasions. For example, if the consumer planned to consume the milk prior to the point when the curve represented by nutritional substance B crosses the curve represented by nutritional substance A, then the consumer should choose the milk represented by nutritional substance B because it has a higher nutritional value until it crosses the curve represented by nutritional substance A. However, if the consumer expects to consume at least some of the milk at a point in time after the time when the curve represented by nutritional substance B crosses the curve represented by nutritional substance A, then the consumer might choose to select the milk represented by the nutritional substance A, even though milk represented by nutritional substance A has a lower nutritional value than the milk represented by nutritional substance B at an earlier time. This change to a desired nutritional value in a nutritional substance over a change in a condition of the nutritional substance described in FIG. 2 can be measured and/or controlled throughout nutritional substance supply system 10 in FIG. 1. This example demonstrates how dynamically generated information regarding a ΔN of a nutritional substance, in this case a change in nutritional value of milk, can be used to understand a rate at which that nutritional value changes or degrades; when that nutritional value expires; and a residual nutritional value of the nutritional substance over a change in a condition of the nutritional substance, in this example a change in time. This ΔN information could further be used to determine a best consumption date for nutritional substance A and B, which could be different from each other depending upon the dynamically generated information generated for each.

In FIG. 1, Creation module 200 can dynamically encode nutritional substances to enable the tracking of changes in nutritional, organoleptic, and/or aesthetic value of the nutritional substance, or ΔN. This dynamic encoding, also referred to herein as a dynamic information identifier, can replace and/or complement existing nutritional substance marking systems such as barcodes, labels, and/or ink markings. This dynamic encoding, or dynamic information identifier, can be used to make nutritional substance information from creation module 200 available to information module 100 for use by preservation module 300, transformation module 400, conditioning module 500, and/or consumption module 600, which includes the ultimate consumer of the nutritional substance. One method of marking the nutritional substance with a dynamic information identifier by creation module 200, or any other module in nutritional supply system 10, could include an electronic tagging system, such as the tagging system manufactured by Kovio of San Jose, Calif., USA. Such thin film chips can be used not only for tracking nutritional substances, by can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow the dynamic nutritional value database of information module 100 real time, or near real time updates about a ΔN of a particular nutritional sub stance.

Preservation module 300 includes packers and shippers of nutritional substances. The tracking of changes in nutritional, organoleptic, and/or aesthetic values, or a ΔN, during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information such as ΔN, an actual expiration date, referred to herein as a dynamic expiration date, can be determined dynamically, and could be significantly later in time than an extrapolated expiration date. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives.

It should be noted that a dynamic expiration date need not be indicated numerically (i.e., as a numerical date) but could be indicated symbolically as by the use of colors—such as green, yellow and red employed on semaphores—or other designations. In those instances, the dynamic expiration date would not be interpreted literally but, rather, as a dynamically-determined advisory date. In practice a dynamic expiration date will be provided for at least one component of a single or multi-component nutritional substance. For multi-component nutritional substances, the dynamic expiration date could be interpreted as a "best" date for consumption for particular components.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, the food processor could include a dynamically generated nutritional value table, also referred to herein as a dynamic nutritional value table, for the actual nutritional substance being supplied. The information in such a dynamic nutritional value table could be used by conditioning module 500 in the preparation of the nutritional substance, and/or used by consumption module 600, so as to allow the ultimate consumer the ability to select the most desirable nutritional substance which meets their needs, and/or to track information regarding nutritional substances consumed.

Information about changes in nutritional, organoleptic, and/or aesthetic values of nutritional substances, or ΔN, is particularly useful in the conditioning module 500 of the present invention, as it allows knowing, or estimating, the pre-conditioning state of the nutritional, organoleptic, and/or aesthetic values of the nutritional substance, and allows for estimation of a ΔN associated with proposed conditioning parameters. The conditioning module 500 can therefore create conditioning parameters, such as by modifying existing or baseline conditioning parameters, to deliver desired nutritional, organoleptic, and/or aesthetic values after conditioning. The pre-conditioning state of the nutritional, organoleptic, and/or aesthetic value of a nutritional substance is not tracked or provided to the consumer by existing conditioners, nor is the ΔN expected from a proposed conditioning tracked or provided to the consumer either before or after conditioning. However, using information provided by information module 100 from creation module 200, preservation module 300, transformation module 400, and/or information measured or generated by conditioning module 500, conditioning module 500 could provide the consumer with the actual, and/or estimated change in nutritional, organoleptic, and/or aesthetic values of the nutritional substance, or ΔN. Further, consumer feedback and updates regarding observed or measured changes in the nutritional, organoleptic, and/or aesthetic value of nutritional substances, or ΔN, can play a role in updating a dynamic nutritional value database with information about the nutritional substances consumers have purchased and/or prepared for consumption, so that the information is available and useful to others in the nutritional substance supply system, such as through reports reflecting the consumer input or through modification of ΔN. Such information regarding the change to nutritional, organoleptic and/or aesthetic value of the nutritional substance, or ΔN, could be provided not only to the consumer, but could also be provided to information module 100 for use by creation module 200, preservation module 300, transformation module 400, so as to track, and possibly improve nutritional substances throughout the entire nutritional substance supply system 10.

The information regarding nutritional substances provided by information module 100 to consumption module 600 can replace or complement existing information sources such as recipe books, food databases like www.epicurious.com, and Epicurious apps. Through the use of specific information regarding a nutritional substance from information module 100, consumers can use consumption module 600 to select nutritional substances according to nutritional, organoleptic, and/or aesthetic values. This will further allow consumers to make informed decisions regarding nutritional substance additives, preservatives, genetic modifications, origins, traceability, and other nutritional substance attributes that may also be tracked through the information module 100. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to optimize nutritional, organoleptic, and/or aesthetic values of a nutritional substance and/or component nutritional substances thereof according to the consumer's needs or preference, and/or minimize degradation of, preserve, or improve nutritional, organoleptic, and/or aesthetic value of a nutritional substance and/or component nutritional substances thereof.

Through the use of nutritional substance information available from information module 100 nutritional substance supply system 10 can track nutritional, organoleptic, and/or aesthetic value. Using this information, nutritional substances travelling through nutritional substance supply system 10 can be dynamically valued and priced according to nutritional, organoleptic, and/or aesthetic values. For example, nutritional substances with longer dynamic expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity. Therefore, both the starting nutritional, organoleptic, and/or aesthetic value and the $\Delta N$ associated with those values are important factors in determining or estimating an actual, or residual, nutritional, organoleptic, and/or aesthetic value of a nutritional substance, and accordingly are important factors in establishing dynamically valued and priced nutritional substances.

During the period of implementation of the present inventions, there will be nutritional substances being marketed including those benefiting from the tracking of dynamic nutritional information such as $\Delta N$, also referred to herein as information-enabled nutritional substances, and nutritional substances which do not benefit from the tracking of dynamic nutritional information such as $\Delta N$, which are not information enabled and are referred to herein as dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances.

For example, the producer of a ready-to-eat dinner would prefer to use corn of a high nutritional, organoleptic, and/or aesthetic value in the production of its product, the ready-to-eat dinner, so as to produce a premium product of high nutritional, organoleptic, and/or aesthetic value. Depending upon the levels of the nutritional, organoleptic, and/or aesthetic values, the ready-to-eat dinner producer may be able to charge a premium price and/or differentiate its product from that of other producers. When selecting the corn to be used in the ready-to-eat dinner, the producer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. And finally, the packager/shipper of preservation module 300 will select corn of high nutritional, organoleptic, and/or aesthetic value from the grower of creation module 200, who will also be able to charge a premium for corn of high nutritional, organoleptic, and/or aesthetic values.

The change to nutritional, organoleptic, and/or aesthetic value for a nutritional substance, or $\Delta N$, tracked through nutritional substance supply system 10 through nutritional substance information from information module 100 can be preferably determined from measured information. However, some or all such nutritional substance $\Delta N$ information may be derived through measurements of environmental conditions of the nutritional substance as it travelled through nutritional substance supply system 10. Additionally, some or all of the nutritional substance $\Delta N$ information can be derived from $\Delta N$ data of other nutritional substances which have travelled through nutritional substance supply system 10. Nutritional substance $\Delta N$ information can also be derived from laboratory experiments performed on other nutritional substances, which may approximate conditions and/or processes to which the actual nutritional substance has been exposed. Further, consumer feedback and updates regarding observed or measured changes in the nutritional, organoleptic, and/or aesthetic value of nutritional substances can play a role in updating $\Delta N$ information.

For example, laboratory experiments can be performed on bananas to determine effect on or change in nutritional, organoleptic, and/or aesthetic value, or $\Delta N$, for a variety of environmental conditions bananas may be exposed to during packaging and shipment in preservation module 300. Using this experimental data, tables and/or algorithms could be developed which would predict the level of change of nutritional, organoleptic, and/or aesthetic values, or $\Delta N$, for a particular banana based upon information collected regarding the environmental conditions to which the banana was exposed during its time in preservation module 300. While the ultimate goal for nutritional substance supply system 10 would be the actual measurement of nutritional, organoleptic, and/or aesthetic values to determine $\Delta N$, use of derived nutritional, organoleptic, and/or aesthetic values from experimental data to determine $\Delta N$ would allow improved logistics planning because it provides the ability to prospectively estimate changes to nutritional, organoleptic, and/or aesthetic values, or $\Delta N$, and because it allows more accurate tracking of changes to nutritional, organoleptic, and/or aesthetic values, or $\Delta N$, while technology and systems are put in place to allow actual measurement.

Figure 3:
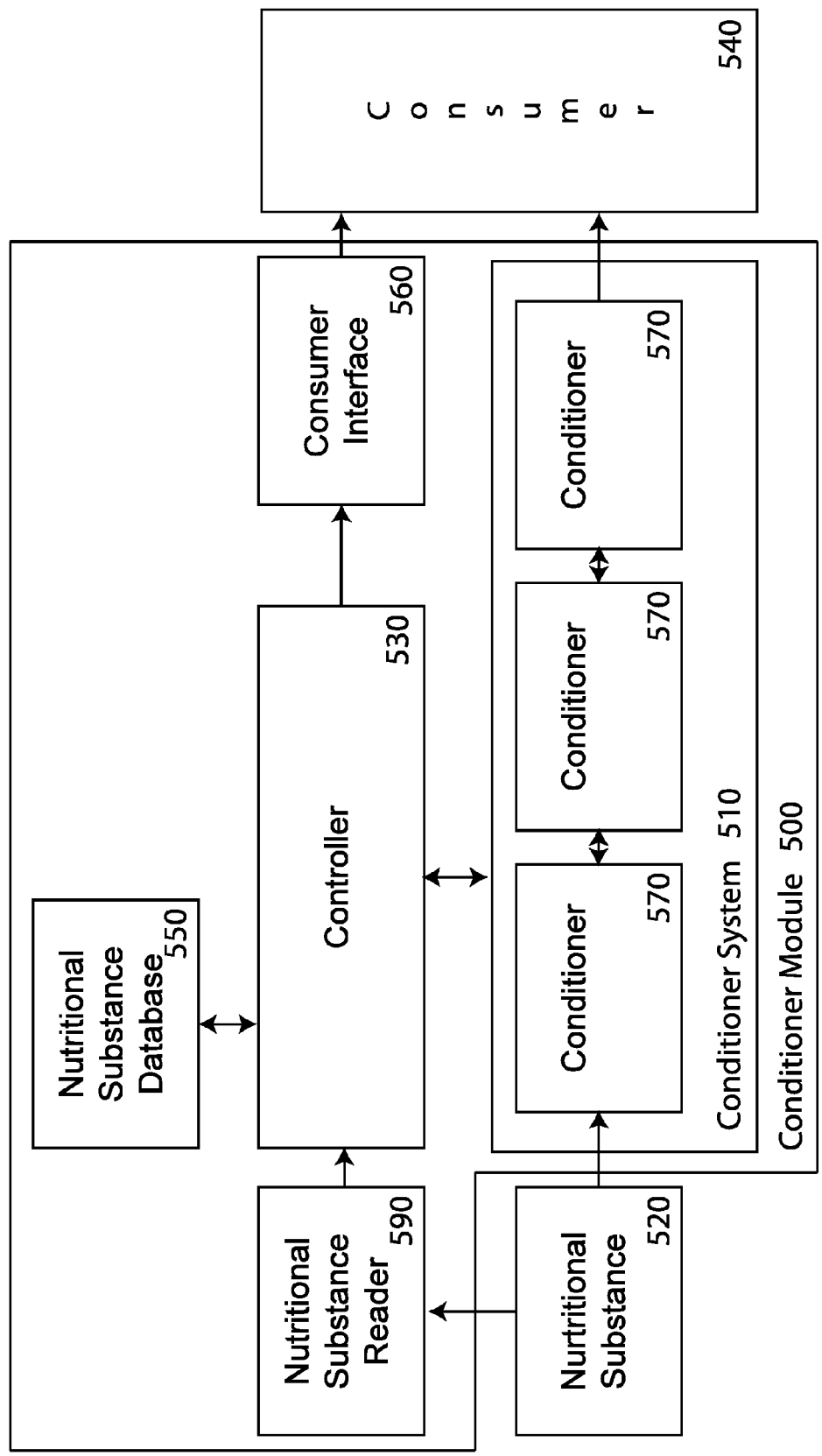
FIG. 3 shows a schematic functional block diagram of the conditioning module 500 according to the present invention.

FIG. 3 shows an embodiment of conditioner module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, although in FIG. 3, it is shown as a separate device. When conditioner system 510 receives nutritional substance 520 for conditioning, nutritional substance reader 590 either receives information regarding nutritional substance 520 and provides it to controller 530, which is the case if the nutritional substance 520 contains a label which includes the information about nutritional substance 520, and/or the nutritional substance reader 590 receives reference information allowing retrieval of the information and provides it to controller 530, which is the case if the nutritional substance 520 is associated with, or provided with a dynamic information identifier. In the case where nutritional substance 520 contains a label which includes the desired information about nutritional substance 520, nutritional substance reader 590 reads this information, provides it to controller 530, which makes it available to consumer 540 by means of consumer interface 560.

For example, if nutritional substance 520 is a ready-to-eat frozen dinner which needs to be heated by conditioner system 510, nutritional substance reader 590 would read a label on nutritional substance 520, thereby receiving the information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that was slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550. Further, linking consumer feedback and updates regarding observed or measured changes in the nutritional, organoleptic, and/or aesthetic values of nutritional substances would provide for virtually real time updates of ΔN information from the actual consumer.

Nutritional substance database 550 could be a database maintained by the transformer of nutritional substance 520 for access by consumers of such nutritional substance 520 to track or estimate changes in the nutritional, organoleptic, and/or aesthetic values of those nutritional substances, as well as any other information about the nutritional substance that can be tracked, including but not limited to the examples previously described. However, preferably, nutritional substance database 550 is a database maintained by the nutritional substance industry for all such information regarding nutritional substances grown, raised, preserved, transformed, conditioned and consumed by consumer 540, in which case it is the database contained within information module 100 and also referred to herein as a dynamic nutritional value database.

It is important to note that while FIGS. 3-6 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558.

In an alternate embodiment of the present invention, controller 530, in addition to providing information regarding nutritional substance 520 to consumer 540, also receives information from conditioner system 510 on how nutritional substance 520 was conditioned. Additionally, conditioner system 510 may also measure or sense information about nutritional substance 520 during its conditioning by conditioner system 510, and provide such information to controller 530, so that such information could also be provided to consumer 540, via consumer interface 560. Further, the controller 530 can receive information from the consumer via consumer interface 560 regarding observed or measured changes in the nutritional, organoleptic, and/or aesthetic values of nutritional substances before or after conditioning, to provide virtually real time updates of ΔN information from the actual consumer, for use by the controller an/or transmission to the nutritional substance database 550.

In a preferred embodiment of the present invention, controller 530 organizes and correlates the information it receives regarding nutritional substance 520 from the various sources of such information, including nutritional substance database 550 and conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs. It could organize information regarding nutritional substance 520 to track consumer's 540 weight loss program. Controller 530 could have access to, or maintain, information regarding consumer 540, so as to track and assist consumer 540 in meeting their specific nutritional needs.

In another embodiment of the present invention conditioner system 510 could be a plurality of conditioner devices which can be selectively operated by controller 530 to prepare nutritional substance 520. Conditioner system 510 can be either a single conditioning device, such as a microwave oven, conventional oven, toaster, blender, steamer, stovetop, or human cook. Conditioner system 510 may be a plurality of conditioners 570. In the case where a plurality of conditioners 570 comprise conditioner system 510, nutritional substance 520 may be manually or automatically transferred between conditioners 570 for eventual transfer to consumer 540.

Nutritional substance reader 590 may be an automatic reader such as a barcode reader or RFID sensor which receives information from nutritional substance 520 or a reference code from nutritional substance 520, such as a dynamic information identifier associated with, or provided with the nutritional substance 520, and provides this information to controller 530. Nutritional substance reader 590 might also be a manual entry system where the reference code, such as a dynamic information identifier associated with, or provided with the nutritional substance 520, is manually entered into nutritional substance reader 590 for use by controller 530, or may alternatively be manually entered into consumer interface 560 for use by controller 530.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

Consumer interface 560 can be implemented as a display device mounted on controller 530, conditioner system 510, or conditioner 570. However, consumer interface 560 is preferably a tablet computer, personal computer, personal assistant, or smart phone, running appropriate software, such as an app.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Figure 4:
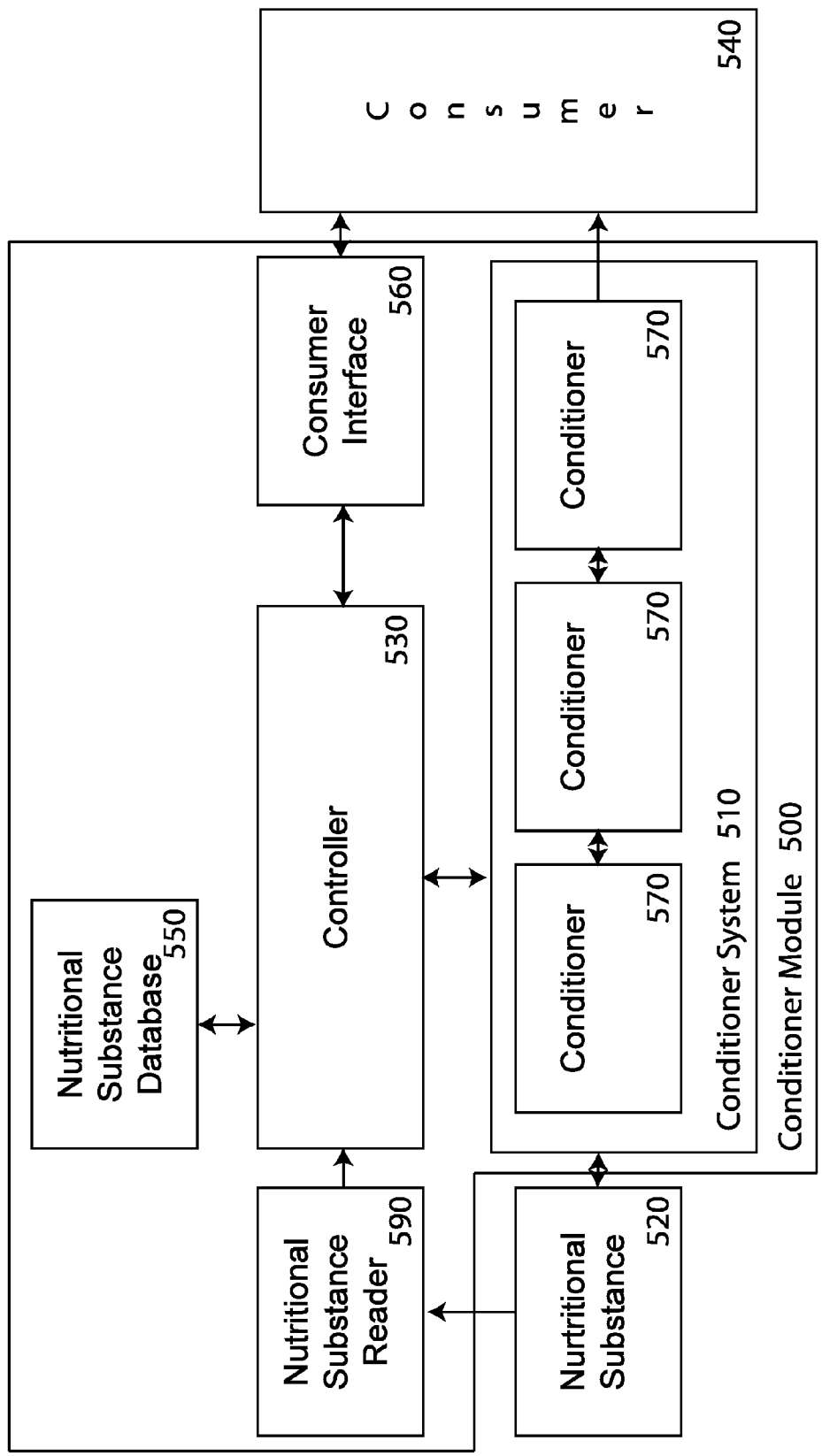
FIG. 4 shows a schematic functional block diagram of the conditioning module 500 according to an alternate embodiment of the present invention.

FIG. 4 shows an embodiment of conditioning module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, although in FIG. 4, it is shown as a separate device. When conditioner system 510 receives nutritional substance 520 for conditioning, nutritional substance reader 590 either receives information regarding nutritional substance 520 and provides it to controller 530, which is the case if the nutritional substance 520 contains a label which includes the information about nutritional substance 520, and/or the nutritional substance reader 590 receives reference information, such as a dynamic information identifier, and provides it to controller 530, allowing retrieval of the information about nutritional substance 520 from nutritional substance database 550, which is the case when the nutritional substance is associated with, or provided with, a dynamic information identifier. In the case where nutritional substance 520 contains a label which includes information about nutritional substance 520, nutritional substance reader 590 reads this information, provides it to controller 530 and makes it available to consumer 540 by means of consumer interface 560.

In an embodiment of the present invention, conditioner system 510 comprises conditioner 570. Conditioner 570 is a conditioning apparatus which can perform a number of operations on nutritional substance 520, separately and/or at the same time. For example, conditioner 570 could be a combination microwave oven, convection oven, grill, and conventional oven. Controller 530 could operate conditioner 570 to execute a sequence of conditioning cycles on nutritional substance 520 to complete its conditioning.

For example, if nutritional substance 520 is a whole frozen turkey to be prepared for dinner, consumer 540 would place the turkey in conditioner 570, the combination cooking unit suggested above. Controller 530 would receive and/or create a protocol of conditioning cycles. Such a protocol could be read by nutritional substance reader 590 from a label on nutritional substance 520. Alternately, a protocol of conditioning cycles could be obtained from nutritional substance database 550 through reference information, such as a dynamic information identifier, obtained by nutritional substance reader 590 from nutritional substance 520. For example, a label on the turkey, could be read by nutritional substance reader 590, providing reference information for the turkey, such as a dynamic information identifier, which controller 530 uses to obtain a conditioning protocol for the turkey from nutritional substance database 550.

An example of such a conditioning protocol for a frozen turkey could be to operate conditioner 570, the combination cooking unit, in the following fashion. First, controller 530 instructs conditioner 570 to use the microwave function of the combination cooking unit to defrost the turkey according to the conditioning protocol obtained for the turkey from nutritional substance database 550 and possibly according to conditioner information provided by conditioner 570, such as the weight of the turkey and information regarding the defrosting process as measured by conditioner 570. Following defrosting of the turkey, controller 530 next instructs the combination cooking unit to operate as a convection oven to cook the turkey, according to the conditioning protocol obtained for the turkey from nutritional substance database 550, for a sufficient length of time so as to ensure that the turkey reaches the proper internal temperature to meet safety requirements, and to maximize organoleptic and/or nutritional properties. Alternatively, the conditioning protocol obtained for the turkey from nutritional substance database 550 may depend upon a direct measurement of the internal temperature of the turkey, or a combination of measured temperature and time. Following the convection oven cooking of the turkey, controller 530 could instruct the combination cooking unit to grill the turkey, according to the conditioning protocol obtained for the turkey from nutritional substance database 550, for a sufficient period of time to create a desirable golden and crispy skin. Alternatively, the conditioning protocol obtained for the turkey from nutritional substance database 550 may depend upon a direct measurement by an optical sensor of external aesthetic values of the turkey such as color, change of color, texture, or change of texture. Alternatively, the conditioning protocol obtained for the turkey from nutritional substance database 550 may depend upon a direct measurement by an infrared sensor of the surface temperature of the turkey, or a combination time, measured aesthetic values, and/or measured surface temperature. Finally, controller 530 could instruct the combination cooking unit to use all three cooking functions at the same time to prepare the turkey for optimal consumption according to the conditioning protocol obtained for the turkey from nutritional substance database 550.

Alternately, conditioner system 510 could be composed of a plurality of conditioners 570. While an automated system for moving a nutritional substance between such conditioners would be optimal, conditioner system 510 could be operated manually by consumer 540 from instructions provided by the controller 530 to consumer interface 560. In this embodiment, controller 530 could provide consumer 540 with instructions as to where to move the turkey after each step in the conditioning protocol. In this example, controller 530 instructs consumer 540 through consumer interface 560 to first place the frozen turkey in conditioner 570, a microwave oven. Controller 530 instructs the microwave oven to defrost the turkey based on information possibly provided by nutritional substance reader 590, nutritional substance database 550 and/or conditioner 570. Upon completion of defrosting by the microwave oven, controller 530 could instruct consumer 540 through interface 560 to move the defrosted turkey from the microwave oven to another conditioner 570, a convection oven. Controller 530 would operate the convection oven to cook the turkey for a sufficient length of time so as to ensure that the turkey reaches the proper internal temperature to meet safety requirements, and to maximize organoleptic and/or nutritional properties. Finally, following the cooking cycle in the convection oven, controller 530 could instruct consumer 540 through consumer interface 560 to move the turkey from the convection oven to another conditioner 570, a grill. Controller 530 would operate the grill so as to grill the turkey for a sufficient period of time to create a desirable golden and crispy skin.

Alternately, conditioner system 510 could be composed of a plurality of conditioners 570; and a consumer 540 (which would include any individuals preparing the turkey for consumption), fulfilling additional conditioner rolls, as will be explained. While an automated system for moving a nutritional substance between such conditioners would be optimal, conditioner system 510 could be operated manually by consumer 540 from instructions provided by a consumer interface 560, which in this case could be a handheld device such as a cellular phone, tablet computer, PDA, or any other device useful for communicating with nutritional substance database 550 and the consumer 540. The handheld device additionally fulfills the roll of nutritional substance reader 590 and controller 530. For example, the consumer 540 can utilize a camera function of the handheld device to read a barcode, or QR code, on or associated with the turkey, wherein the code provides a dynamic information identifier. The handheld device can then use the dynamic information identifier to retrieve information regarding the turkey from nutritional substance database 550. In this example, consumer 540 utilizes the handheld device to read a barcode (or any other readable code) on the turkey, the barcode containing a dynamic information identifier associated with information regarding the turkey within the nutritional substance database 550. The consumer 540 uses the handheld device to retrieve and review a conditioning protocol from nutritional substance database 550, and is accordingly instructed as to where to move the turkey for each step in the conditioning protocol and further instructed on the conditioning parameters required for each step of the conditioning protocol. In this example, consumer 540 retrieves and reviews a conditioning protocol from nutritional substance database 550 using the handheld device and is instructed to first place the frozen turkey in conditioner 570, a microwave oven, and further instructed on conditioning parameters for the microwave oven to defrost the turkey based. Consumer 540 is instructed that upon completion of defrosting by the microwave oven, the turkey is to be moved to another conditioner 570, a convection oven. Consumer 540 is further instructed on conditioning parameters for the convection oven to cook the turkey for a sufficient length of time so as to ensure that the turkey reaches the proper internal temperature to meet safety requirements, and to maximize organoleptic and/or nutritional properties. Finally, consumer 540 is instructed that upon completion of cooking by the convection oven, the turkey is to be moved to another conditioner 570, a grill, and further instructed on conditioning parameters for the grill so as to grill the turkey for a sufficient period of time to create a desirable golden and crispy skin.

In the case where conditioner system 510 is a plurality of conditioners 570, it would also be possible for controller 530 to manage conditioners 570 within conditioner system 510 so as to produce a complete meal. For example, controller 530 could select conditioning protocols which would maximize the use of each conditioner 570. For example, in a meal comprising a turkey, home baked bread, and acorn squash, controller 530 could stage and operate the microwave oven, convection oven, and grill to minimize preparation time for the meal by determining which item should be cooked in which conditioner 570, in which order, to maximize usage of each conditioner 570 in conditioning system 510. In this example, while the turkey is being defrosted in the microwave oven, controller 530 could instruct consumer 540 through interface 560 to place the bread dough in the convection oven and the acorn squash on the grill. Following the defrosting of the turkey, when the turkey is moved to the convection oven, which finished baking the bread, the bread could be moved to the grill for browning, and the acorn squash could be moved to microwave oven to keep warm until the entire meal is ready.

For example, if nutritional substance 520 is a ready-to-eat frozen dinner which needs to be heated by conditioner system 510, nutritional substance reader 590 would read a label on nutritional substance 520, thereby receiving information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that was slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550. Further, linking consumer feedback and updates regarding observed or measured changes in the nutritional, organoleptic, and/or aesthetic values of nutritional substances would provide for virtually real time updates of $\Delta N$ information from the actual consumer.

Nutritional substance database 550 could be a database maintained by the transformer of nutritional substance 520 for access by consumers of such nutritional substance 520 to track or estimate changes in the nutritional, organoleptic, and/or aesthetic values of those nutritional substances, as well as any other information about the nutritional substance that can be tracked, including but not limited to the examples previously described. However, preferably, nutritional substance database 550 is a database within information module 100 that is maintained by the nutritional substance industry for all such information regarding nutritional substances grown, raised, preserved, transformed, conditioned and consumed by consumer 540, in which case it is the database contained within information module 100 and also referred to herein as a dynamic nutritional value database.

In an alternate embodiment of the present invention, controller 530, in addition to providing information regarding nutritional substance 520 to consumer 540, also receives information from conditioner system 510 on how nutritional substance 520 was conditioned. Additionally, conditioner system 510 may also measure or sense information about nutritional substance 520 during its conditioning by conditioner system 510, and provide such information to controller 530, so that such information could also be provided to consumer 540, via consumer interface 560.

In a preferred embodiment of the present invention, controller 530 organizes and correlates the information it receives regarding nutritional substance 520 from the various sources of such information, including nutritional substance database 550 and conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs before or after conditioning, or how it meets the consumer's needs based on various proposed conditioning parameters. It could organize information regarding nutritional substance 520 to track consumer's 540 weight loss program. Controller 530 could have access to, or maintain, information regarding consumer 540, so as to track and assist consumer 540 in meeting their specific nutritional needs.

In another embodiment of the present invention conditioner system 510 could be a plurality of conditioner devices which can be selectively operated by controller 530 to prepare nutritional substance 520. Conditioner system 510 can be either a single conditioning device, such as a microwave oven, conventional oven, toaster, blender, steamer, stovetop, or human cook. Conditioner system 510 may be a plurality of conditioners 570. In the case where a plurality of conditioners 570 comprise conditioner system 510, nutritional substance 520 may be manually or automatically transferred between conditioners 570 for eventual transfer to consumer 540.

Nutritional substance reader 590 may be an automatic reader such as a barcode reader or RFID sensor which receives information from nutritional substance 520 or a reference code from nutritional substance 520, such as a dynamic information identifier, and provides this information to controller 530. Nutritional substance reader 590 might also be a manual entry system where the reference code, such as a dynamic information identifier associated with, or provided with the nutritional substance 520 is manually entered into nutritional substance reader 590 for controller 530.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

It is important to note that while FIGS. 3-6 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Consumer interface 560 can be implemented as a display device mounted on controller 530, conditioner system 510, or conditioner 570. However, consumer interface 560 is preferably a tablet computer, personal computer, personal assistant, or smart phone, running appropriate software, such as an app.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Additionally, controller 530 uses nutritional substance information retrieved by nutritional substance reader 590 from nutritional substance 520, or retrieved from nutritional substance database 550 using reference information obtained by nutritional substance reader 590 from nutritional substance 520, to dynamically modify the operation of conditioner system 510 to maintain organoleptic and nutritional properties of nutritional substance 520. For example, if the nutritional substance 520 is a ready-to-eat dinner, controller 530 could modify the instructions to conditioner system 530 in response to information regarding the corn used in the ready-to-eat dinner such that a temperature and cooking duration can be modified to affect the organoleptic, nutritional, taste, and/or appearance of the corn.

In an embodiment of the present invention, the label on nutritional substance 520 could contain the conditioning instructions for nutritional substance 520, or a reference, such as a dynamic information identifier, to such conditioning instructions in nutritional substance database 550. In operation, this would allow controller 530 to obtain information about nutritional substance 520 on how to dynamically operate conditioner system 510 to condition nutritional substance 520, without consumer intervention. Additionally, conditioning instructions for nutritional substance 520 could be provided for a variety of different conditioner systems 510, or conditioners 570, and controller could select the proper conditioning instructions.

In a further embodiment of the present invention, nutritional substance reader 590 and/or conditioner system 510 measures or senses information about the current state of nutritional substance 520 and provides such information to controller 530 to allow controller 530 to dynamically modify operation of conditioner system 510.

In an additional embodiment of the present invention, consumer 540 provides information regarding their needs and/or desires with regard to the nutritional substance 520 to consumer interface 560. Consumer interface 560 provides this information to controller 530 so as to allow controller 530 to dynamically modify conditioning parameters used by conditioner system 510 in the conditioning of nutritional substance 520, or to request from nutritional substance database 550 dynamically modified conditioning parameters to be used by conditioner system 510 in the conditioning of nutritional substance 520. Consumer's 540 needs and/or desires could include nutritional parameters, taste parameters, aesthetic parameters. For example, consumer 540 may have needs for certain nutrients which are present in nutritional substance 520 prior to conditioning. Controller 530 could modify operation of conditioner system 510 so as to preserve such nutrients. For example, conditioner system 500 can cook the nutritional substance at a lower temperature and/or for a shorter duration so as to minimize nutrient loss. The consumer's 540 needs and/or desires may be related to particular nutritional, organoleptic, an/or aesthetic values, and may additionally be related to other nutritional substance attributes that are retrievable through the nutritional substance database 550 using a dynamic information identifier, such as nutritional substance additives, preservatives, genetic modifications, origins, and traceability. Further, the consumer's needs and/or desires could be part of a consumer profile provided to the controller 530 through the consumer interface 560 or otherwise available to controller 530. The consumer's needs and/or desires could be exclusionary in nature, for example no products of animal origin, no peanuts or peanut-derived products, no farm raised products, no pork products, or no imported products. In these cases, the nutritional substance database 550 could provide information that would prevent the consumer from preparing and/or consuming products that the consumer cannot, should not, or prefers not to consume.

The consumer's 540 organoleptic and/or aesthetic desires could include how rare or well done they prefer a particular nutritional substance to be prepared. For example, consumer 540 may prefer his vegetables to be crisp or pasta to be prepared al dente. With such information provided by consumer 540 to controller 530 through consumer interface 560, controller 530 can dynamically modify operation of conditioner system 510 responsive to the consumer information and provide a nutritional substance according to the consumer's desires.

In the preferred embodiment of the present invention, controller 530 receives information regarding the history of nutritional substance 520, current information on nutritional substance 520, and consumer 540 needs and/or desires, and dynamically modifies operation of conditioner system 510 responsive to the information so as to provide a nutritional substance according to the consumer's needs and/or desires. For example, if nutritional substance 520 is a steak, controller 530 would receive reference information regarding the steak, nutritional substance 520, from nutritional substance reader 590. Controller 530 would use this reference information to obtain information about the steak from nutritional substance database 550. Controller 530 could also receive current information about the steak from nutritional substance reader 590 and/or conditioner 510. Additionally, controller 530 could receive consumer 540 preferences from consumer interface 560. Finally, controller 530 could receive information from conditioner system 510 during the conditioning of the steak, nutritional substance 520. Using some or all of such information, controller 530 would dynamically modify the cooking of the steak to preserve, optimize, or enhance organoleptic, nutritional, and aesthetic properties to meet consumer 540 needs. For example, the steak could be cooked slowly to preserve iron levels within the meat, and also cooked to well-done to meet consumer's 540 taste.

Figure 5:
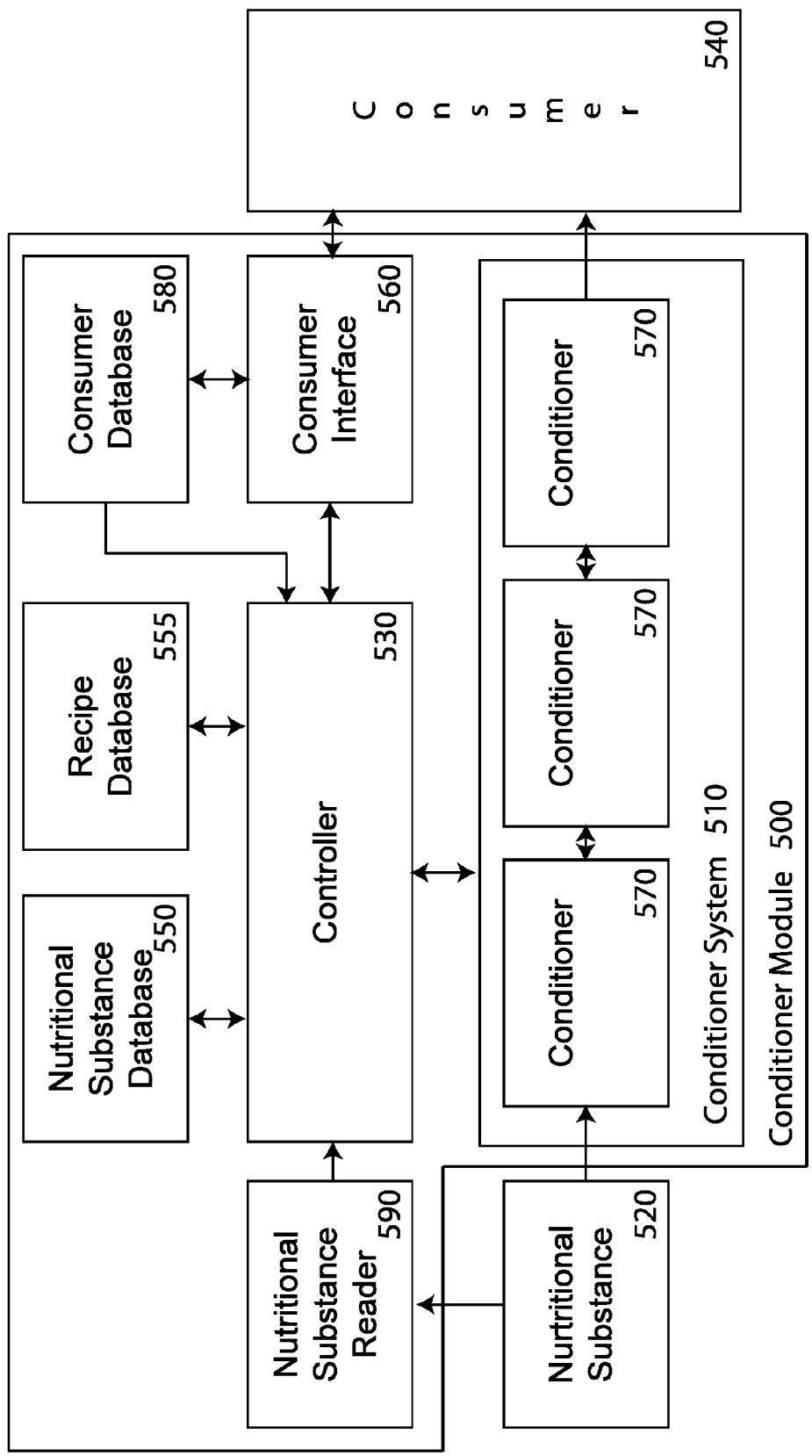
FIG. 5 shows a schematic functional block diagram of the conditioning module 500 according to an alternate embodiment of the present invention.

FIG. 5 shows an embodiment of conditioning module 500 of the present invention. Conditioner system 510 receives nutritional substance 520 for conditioning before it is delivered to consumer 540. Controller 530 is operably connected to conditioner system 510. In fact, controller 530 may be integrated within conditioner system 510, although in FIG. 5, it is shown as a separate device. When conditioner system 510 receives nutritional substance 520 for conditioning, nutritional substance reader 590 either receives information regarding nutritional substance 520 and provides it to controller 530, which is the case if the nutritional substance 520 contains a label which includes the information about nutritional substance 520, and/or the nutritional substance reader 590 receives reference information, such as a dynamic information identifier, and provides it to controller 530, allowing retrieval of the information about nutritional substance 520 from nutritional substance database 550, which is the case when the nutritional substance is associated with, or provided with, a dynamic information identifier. In the case where nutritional substance 520 contains a label which includes information about nutritional substance 520, nutritional substance reader 590 reads this information, provides it to controller 530 and makes it available to consumer 540 by means of consumer interface 560.

In an embodiment of the present invention, conditioner system 510 comprises conditioner 570. Conditioner 570 is a conditioning apparatus which can perform a number of operations on nutritional substance 520, separately and/or at the same time. For example, conditioner 570 could be a combination microwave oven, convection oven, grill, and conventional oven. Controller 530 could operate conditioner 570 to execute a sequence of conditioning cycles on nutritional substance 520 to complete its conditioning.

For example, if nutritional substance 520 is a whole frozen turkey to be prepared for dinner, consumer 540 would place the turkey in conditioner 570, the combination cooking unit suggested above. Controller 530 would receive and/or create a protocol of conditioning cycles. Such a protocol could be read by nutritional substance reader 590 from a label on nutritional substance 520. Alternately, a protocol of conditioning cycles could be obtained from nutritional substance database 550 through reference information such as a dynamic information identifier, obtained by nutritional substance reader 590 from nutritional substance 520. For example, a label on the turkey could be read by nutritional substance reader 590, providing reference information for the turkey, such as a dynamic information identifier, which controller 530 uses to obtain a conditioning protocol for the turkey from nutritional substance database 550.

An example of such a conditioning protocol for a frozen turkey could be to operate conditioner 570, the combination cooking unit in the following fashion. First, controller 530 instructs conditioner 570 to use the microwave function of the combination cooking unit to defrost the turkey according to the conditioning protocol obtained for the turkey from nutritional substance database 550 and possibly according to conditioner information provided by conditioner 570, such as the weight of the turkey and information regarding the defrosting process as measured by conditioner 570. Following defrosting of the turkey, controller 530 next instructs the combination cooking unit to operate as a convection oven to cook the turkey, according to the conditioning protocol obtained for the turkey from nutritional substance database 550, for a sufficient length of time so as to ensure that the turkey reaches the proper internal temperature to meet safety requirements, and to maximize organoleptic and/or nutritional properties. Alternatively, the conditioning protocol obtained for the turkey from nutritional substance database 550 may depend upon a direct measurement of the internal temperature of the turkey, or a combination of measured temperature and time. Following the convection oven cooking of the turkey, controller 530 could instruct the combination cooking unit to grill the turkey, according to the conditioning protocol obtained for the turkey from nutritional substance database 550, for a sufficient period of time to create a desirable golden and crispy skin. Alternatively, the conditioning protocol obtained for the turkey from nutritional substance database 550 may depend upon a direct measurement by an optical sensor of external aesthetic values of the turkey such as color, change of color, texture, or change of texture. Alternatively, the conditioning protocol obtained for the turkey from nutritional substance database 550 may depend upon a direct measurement by an infrared sensor of the surface temperature of the turkey, or a combination time, measured aesthetic values, and/or measured surface temperature. Finally, controller 530 could instruct the combination cooking unit to use all three cooking functions at the same time to prepare the turkey for optimal consumption according to the conditioning protocol obtained for the turkey from nutritional substance database 550.

Alternately, conditioner system 510 could be composed of a plurality of conditioners 570. While an automated system for moving a nutritional substance between such conditioners would be optimal, conditioner system 510 could be operated manually by consumer 540 from instructions provided by the controller 530 to consumer interface 560. In this embodiment, controller 530 could provide consumer 540 with instructions as to where to move the turkey after each step in the conditioning protocol. In this example, controller 530 instructs consumer 540 through consumer interface 560 to first place the frozen turkey in conditioner 570, a microwave oven. Controller 530 instructs the microwave oven to defrost the turkey based on information possibly provided by nutritional substance reader 590, nutritional substance database 550 and/or conditioner 570. Upon completion of defrosting by the microwave oven, controller 530 could instruct consumer 540 through interface 560 to move the defrosted turkey from the microwave oven to another conditioner 570, a convection oven. Controller 530 would operate the convection oven to cook the turkey for a sufficient length of time so as to ensure that the turkey reaches the proper internal temperature to meet safety requirements, and to maximize organoleptic and/or nutritional properties. Finally, following the cooking cycle in the convection oven, controller 530 could instruct consumer 540 through consumer interface 560 to move the turkey from the convection oven to another conditioner 570, a grill. Controller 530 would operate the grill so as to grill the turkey for a sufficient period of time to create a desirable golden and crispy skin.

Alternately, conditioner system 510 could be composed of a plurality of conditioners 570; and a consumer 540 (which would include any individuals preparing the turkey for consumption), fulfilling additional conditioner rolls, as will be explained. While an automated system for moving a nutritional substance between such conditioners would be optimal, conditioner system 510 could be operated manually by consumer 540 from instructions provided by a consumer interface 560, which in this case could be a handheld device such as a cellular phone, tablet computer, PDA, or any other device useful for communicating with nutritional substance database 550 and the consumer 540. The handheld device additionally fulfills the roll of nutritional substance reader 590 and controller 530. For example, the consumer 540 can utilize a camera function of the handheld device to read a barcode, or QR code, on or associated with the turkey, wherein the code provides a dynamic information identifier. The handheld device can then use the dynamic information identifier to retrieve information regarding the turkey from nutritional substance database 550. In this example, consumer 540 utilizes the handheld device to read a barcode (or any other readable code) on the turkey, the barcode containing a dynamic information identifier associated with information regarding the turkey within the nutritional substance database 550. The consumer 540 uses the handheld device to retrieve and review a conditioning protocol from nutritional substance database 550, and is accordingly instructed as to where to move the turkey for each step in the conditioning protocol and further instructed on the conditioning parameters required for each step of the conditioning protocol. In this example, consumer 540 retrieves and reviews a conditioning protocol from nutritional substance database 550 using the handheld device and is instructed to first place the frozen turkey in conditioner 570, a microwave oven, and further instructed on conditioning parameters for the microwave oven to defrost the turkey based. Consumer 540 is instructed that upon completion of defrosting by the microwave oven, the turkey is to be moved to another conditioner 570, a convection oven. Consumer 540 is further instructed on conditioning parameters for the convection oven to cook the turkey for a sufficient length of time so as to ensure that the turkey reaches the proper internal temperature to meet safety requirements, and to maximize organoleptic and/or nutritional properties. Finally, consumer 540 is instructed that upon completion of cooking by the convection oven, the turkey is to be moved to another conditioner 570, a grill, and further instructed on conditioning parameters for the grill so as to grill the turkey for a sufficient period of time to create a desirable golden and crispy skin.

In the case where conditioner system 510 is a plurality of conditioners 570, it would also be possible for controller 530 to manage conditioners 570 within conditioner system 510 so as to produce a complete meal. For example, controller 530 could select conditioning protocols which would maximize the use of each conditioner 570. For example, in a meal comprising a turkey, home baked bread, and acorn squash, controller 530 could stage and operate the microwave oven, convection oven, and grill to minimize preparation time for the meal by determining which item should be cooked in which conditioner 570, in which order, to maximize usage of each conditioner 570 in conditioning system 510. In this example, while the turkey is being defrosted in the microwave oven, controller 530 could instruct consumer 540 through interface 560 to place the bread dough in the convection oven and the acorn squash on the grill. Following the defrosting of the turkey, when the turkey is moved to the convection oven, which finished baking the bread, the bread could be moved to the grill for browning, and the acorn squash could be moved to microwave oven to keep warm, until the entire meal is ready.

For example, if nutritional substance 520 is a ready-to-eat frozen dinner which needs to be heated by conditioner system 510, nutritional substance reader 590 would read a label on nutritional substance 520 thereby receiving information regarding nutritional substance 520, and then provide the information to controller 530. This information could include creation information as to the creation of the various components which constitute the ready-to-eat dinner. This information could include information about where and how the corn in the ready-to-eat dinner was grown, including the corn seed used, where it was planted, how it was planted, how it was irrigated, when it was picked, and information on fertilizers and pesticides used during its growth. Additionally, this information could include the cattle lineage, health, immunization, dietary supplements that were fed to the cattle that was slaughtered to obtain the beef in the ready-to-eat dinner.

The information from a label on nutritional substance 520 could also include information on how the components were preserved for shipment from the farm or slaughterhouse on their path to the nutritional substance transformer who prepared the ready-to-eat dinner. Additional information could include how the nutritional substance transformer transformed the components into the ready-to-eat dinner, such as recipe used, additives to the dinner, and actual measured conditions during the transformation into the ready-to-eat dinner.

While such information could be stored on a label located on the packaging for nutritional substance 520 so as to be read by nutritional substance reader 590, provided to controller 530, and provided to consumer interface 560 for display to consumer 540, preferably, the label on the nutritional substance package includes reference information, such as a dynamic information identifier, which is read by nutritional substance reader 590 and provided to controller 530 that allows controller 530 to retrieve the information about nutritional substance 520 from nutritional substance database 550. Further, linking consumer feedback and updates regarding observed or measured changes in the nutritional, organoleptic, and/or aesthetic values of nutritional substances would provide for virtually real time updates of ΔN information from the actual consumer.

Nutritional substance database 550 could be a database maintained by the transformer of nutritional substance 520 for access by consumers of such nutritional substance 520 to track or estimate changes in the nutritional, organoleptic, and/or aesthetic values of those nutritional substances, as well as any other information about the nutritional substance that can be tracked, including but not limited to the examples previously described. However, preferably, nutritional substance database 550 is a database within information module 100 that is maintained by the nutritional substance industry for all such information regarding nutritional substances grown, raised, preserved, transformed, conditioned and consumed by consumer 540, in which case it is the database contained within information module 100 and also referred to herein as a dynamic nutritional value database.

In an alternate embodiment of the present invention, controller 530, in addition to providing information regarding nutritional substance 520 to consumer 540, also receives information from conditioner system 510 on how nutritional substance 520 was conditioned. Additionally, conditioner system 510 may also measure or sense information about nutritional substance 520 during its conditioning by conditioner system 510, and provide such information to controller 530, so that such information could also be provided to consumer 540, via consumer interface 560.

In a preferred embodiment of the present invention, controller 530 organizes and correlates the information it receives regarding nutritional substance 520 from the various sources of such information, including nutritional substance database 550 and conditioner system 510, and presents such information through consumer interface 560 to consumer 540 in a manner useful to consumer 540. For example, such information may be provided in a manner that assists consumer 540 in understanding how nutritional substance 520 meets consumer's 540 nutritional needs before or after conditioning, or how it meets the consumer's needs based on various proposed conditioning parameters. It could organize information regarding nutritional substance 520 to track consumer's 540 weight loss program. Controller 530 could have access to, or maintain, information regarding consumer 540, so as to track and assist consumer 540 in meeting their specific nutritional needs.

In another embodiment of the present invention conditioner system 510 could be a plurality of conditioner devices which can be selectively operated by controller 530 to prepare nutritional substance 520. Conditioner system 510 can be either a single conditioning device, such as a microwave oven, conventional oven, toaster, blender, steamer, stovetop, or human cook. Conditioner system 510 may be a plurality of conditioners 570. In the case where a plurality of conditioners 570 comprise conditioner system 510, nutritional substance 520 may be manually or automatically transferred between conditioners 570 for eventual transfer to consumer 540.

Nutritional substance reader 590 may be an automatic reader such as a barcode reader or RFID sensor which receives information from nutritional substance 520 or a reference code from nutritional substance 520, such as a dynamic information identifier, and provides this information to controller 530. Nutritional substance reader 590 might also be a manual entry system where the reference code, such as a dynamic information identifier associated with, or provided with the nutritional substance 520 is manually entered into nutritional substance reader 590 for controller 530.

Nutritional substance database 550 could be a flat database, relational database or, preferably, a multi-dimensional database. Nutritional substance database 550 could be local but, preferably, it would be located remotely, such as on the internet, and accessed via a telecommunication system, such as a wireless telecommunication system. Controller 530 can be implemented using a computing device, such as a microcontroller, micro-processor, personal computer, or tablet computer. Controller 530 could be integrated to include nutritional substance reader 590, consumer interface 560, and/or nutritional substance database 550. Additionally, controller 530 may be integrated in conditioner system 510, including integration into conditioner 570.

It is important to note that while FIGS. 3-6 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Consumer interface 560 can be implemented as a display device mounted on controller 530, conditioner system 510, or conditioner 570. However, consumer interface 560 is preferably a tablet computer, personal computer, personal assistant, or smart phone, running appropriate software, such as an app.

While conditioner module 500 can be located in the consumer's home, conditioner module 500 may be located at a restaurant or other food service establishment for use in preparing nutritional substances 520 for consumers who patronize such an establishment. Additionally, conditioner module 500 could be located at a nutritional substance seller such as a grocery store or health food store for preparation of nutritional substances 520 purchased by consumers at such an establishment. It could be foreseen that conditioner modules 500 could become standalone businesses where consumers select nutritional substances for preparation at the establishment or removal from the establishment for consumption elsewhere.

Additionally, controller 530 uses nutritional substance information retrieved by nutritional substance reader 590 from nutritional substance 520, or retrieved from nutritional substance database 550 using reference information obtained by nutritional substance reader 590 from nutritional substance 520, to dynamically modify the operation of conditioner system 510 to maintain organoleptic and nutritional properties of nutritional substance 520. For example, if the nutritional substance 520 is a ready-to-eat dinner, controller 530 could modify the instructions to conditioner system 530 in response to information regarding the corn used in the ready-to-eat dinner such that a temperature and cooking duration can be modified to affect the organoleptic, nutritional, taste, and/or appearance of the corn.

In an embodiment of the present invention, the label on nutritional substance 520 could contain the conditioning instructions for nutritional substance 520, or a reference, such as a dynamic information identifier, to such conditioning instructions in nutritional substance database 550. In operation, this would allow controller 530 to obtain information about nutritional substance 520 on how to dynamically operate conditioner system 510 to condition nutritional substance 520, without consumer intervention. Additionally, conditioning instructions for nutritional substance 520 could be provided for a variety of different conditioner systems 510, or conditioners 570, and controller could select the proper conditioning instructions.

In a further embodiment of the present invention, nutritional substance reader 590 and/or conditioner system 510 measures or senses information about the current state of nutritional substance 520 and provides such information to controller 530 to allow controller 530 to dynamically modify operation of conditioner system 510.

In an additional embodiment of the present invention, consumer 540 provides information regarding their needs and/or desires with regard to the nutritional substance 520 to consumer interface 560. Consumer interface 560 provides this information to controller 530 so as to allow controller 530 to dynamically modify conditioning parameters used by conditioner system 510 in the conditioning of nutritional substance 520, or to request from nutritional substance database 550 dynamically modified conditioning parameters to be used by conditioner system 510 in the conditioning of nutritional substance 520. Consumer's 540 needs and/or desires could include nutritional parameters, taste parameters, aesthetic parameters. For example, consumer 540 may have needs for certain nutrients which are present in nutritional substance 520 prior to conditioning. Controller 530 could modify operation of conditioner system 510 so as to preserve such nutrients. For example, conditioner system 500 can cook the nutritional substance at a lower temperature and/or for a shorter duration so as to minimize nutrient loss. The consumer's 540 needs and/or desires may be related to particular nutritional, organoleptic, an/or aesthetic values, and may additionally be related to other nutritional substance attributes that are retrievable through the nutritional substance database 550 using a dynamic information identifier, such as nutritional substance additives, preservatives, genetic modifications, origins, and traceability. Further, the consumer's needs and/or desires could be part of a consumer profile provided to the controller 530 through the consumer interface 560 or otherwise available to controller 530. The consumer's needs and/or desires could be exclusionary in nature, for example no products of animal origin, no peanuts or peanut-derived products, no farm raised products, no pork products, or no imported products. In these cases, the nutritional substance database 550 could provide information that would prevent the consumer from preparing and/or consuming products that the consumer cannot, should not, or prefers not to consume.

The consumer's 540 organoleptic and/or aesthetic desires could include how rare or well done they prefer a particular nutritional substance to be prepared. For example, consumer 540 may prefer his vegetables to be crisp or pasta to be prepared al dente. With such information provided by consumer 540 to controller 530 through consumer interface 560, controller 530 can dynamically modify operation of conditioner system 510 responsive to the consumer information and provide a nutritional substance according to the consumer's desires.

In the preferred embodiment of the present invention, controller 530 receives information regarding the history of nutritional substance 520, current information on nutritional substance 520, and consumer 540 needs and/or desires, and dynamically modifies operation of conditioner system 510 responsive to the information so as to provide a nutritional substance according to the consumer's needs and/or desires. For example, if nutritional substance 520 is a steak, controller 530 would receive reference information, such as a dynamic information identifier, regarding the steak, nutritional substance 520, from nutritional substance reader 590. Controller 530 would use this reference information to obtain information about the steak from nutritional substance database 550. Controller 530 could also receive current information about the steak from nutritional substance reader 590 and/or conditioner 510. Additionally, controller 530 could receive consumer 540 preferences from consumer interface 560. Finally, controller 530 could receive information from conditioner system 510 during the conditioning of the steak, nutritional substance 520. Using some or all of such information, controller 530 would dynamically modify the cooking of the steak to preserve optimize, or enhance organoleptic, nutritional, and aesthetic properties to meet consumer 540 needs. For example, the steak could be cooked slowly to preserve iron levels within the meat, and also cooked to well-done to meet consumer's 540 taste.

Conditioner system 510 can prepare a nutritional substance for consumer 540 which contains a plurality of nutritional substances 520. Conditioner module 500 includes recipe database 555 which is operably connected to controller 530. Recipe database 555 can be part of nutritional substance database 550, or it can be a stand-alone database. While recipe database 555 can be located locally, it is preferably accessible to many conditioner modules 500 through a telecommunications system such as the internet, including wireless telecommunications systems.

Controller 530 is also preferably connected to consumer database 580. Consumer database 580 may be additionally connected to consumer interface 560. Consumer database 580 could include consumer's 540 organoleptic and nutritional needs, and consumer 540 preferences, and could be in the form of a consumer profile custom tailored to an individual consumer or selected from a menu of consumer profiles. Consumer database 580 may receive input regarding consumer 540 from consumer 540, but could also include information supplied by consumer's 540 medical records, exercise records for the consumer's gym, and other information sources. Consumer database 580 could include information regarding regulatory actions and/or manufacturer warnings or recalls of nutritional substances which may be obtained, have been obtained, or may be prepared or consumed by the consumer. Additionally, consumer database 580 could include information regarding consumer's 540 preferences provided by controller 530 for previous nutritional substance 520 conditionings. Finally, consumer database 580 could include consumer preferences from external sources such as restaurants and grocery stores where consumer 540 purchases nutritional substances 520. Finally, consumer database 580 could include information from consumer module 600, in FIG. 1.

Consumer database 580 could be a local database maintained by controller 530 and/or consumer interface 560. Preferably, consumer database 580 is part of a nutritional substance industry database containing such information regarding a plurality of consumers 540.

For example, controller 530 can operate to select the necessary ingredients, nutritional substance 520, to prepare a meal. In this case, nutritional substance 520 could be a plurality of nutritional substances 520. In operation, consumer 540 could select a dinner menu using consumer interface 560. Additionally, consumer 540 could select a specific recipe from recipe database 555 or could select a recipe source within database 555, such as low salt meals and/or recipes by a certain well-known chef. Controller 530 could prepare a shopping list for consumer 540 through consumer interface 560. Alternatively, controller 530 could transmit a shopping list to a nutritional substance 520 supplier such as a grocery store, so consumer 540 could pick up such items already selected or could have such items delivered.

Alternatively, if instructed by consumer 540 to utilize nutritional substances on hand, which have been logged into controller 530 through nutritional substance reader 590, controller 530 could modify or suggest a recipe that used only nutritional substances 520 available to conditioner module 500. For example, if consumer 540 instructs conditioner module 500 through conditioner interface 560 that consumer 540 would like Italian food in the style of a well-known Italian chef, controller 530 would utilize information in its various databases to prepare such a meal. In this case, controller 530 would match its inventory of available nutritional substances with recipes from the well-known Italian chef in recipe database 555 and find available recipes. Controller 530 could select a recipe that optimized consumer's 540 needs and preferences and prepare a meal using conditioner system 510. Alternatively, controller 530 could present various options to consumer 540 using consumer interface 560, highlighting features of each available meal from the standpoint of consumer's 540 nutritional needs and/or preferences.

Figure 6:
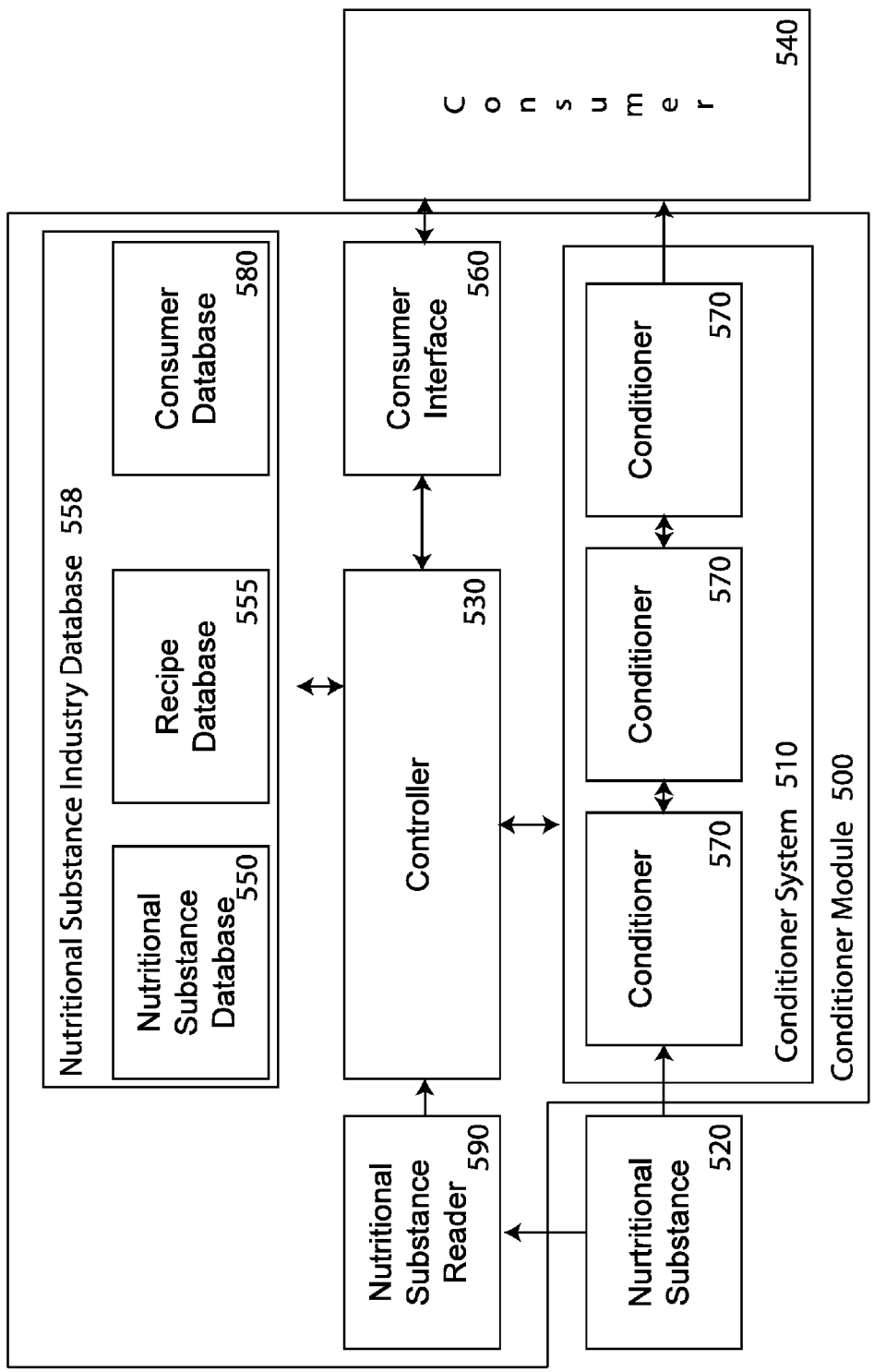
FIG. 6 shows a schematic functional block diagram of the conditioning module 500 according to an alternate embodiment of the present invention.

In FIG. 6, nutritional substance database 550, recipe database 555, and consumer database 580 are part of nutritional substance industry database 558. Controller 530 would communicate with nutritional substance industry database 558 through a communication system such as the internet, and preferably a telecommunications system such as wireless telecommunications.

It is important to note that while FIGS. 3-6 of various embodiments of the present invention show nutritional substance database 550 as part of the conditioner module 500, they are in no way limited to this interpretation. It is understood that this convention is only one way of illustrating the inventions described herein, and it is further understood that this is in no way limiting to the scope of the present invention. The same is understood for recipe database 555, consumer database 580, and nutritional substance industry database 558. For example, any of nutritional substance database 550, recipe database 555, consumer database 580, and nutritional substance industry database 558 can be contained within information module 100 or within conditioner module 500.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. §112, sixth paragraph, other aspects may likewise be embodied as a means-plus-function claim, or in other forms, such as being embodied in a computer-readable medium. Any claims intended to be treated under 35 U.S.C. §112, ¶6 will begin with the words "means for." Accordingly, the applicant reserves the right to add additional claims after filing the application to pursue such additional claim forms for other aspects of the invention.

The invention claimed is:

1. A method of dynamically conditioning nutritional substances comprising steps of:
   accessing a nutritional substance database containing (a) information related to nutritional substances prior to conditioning and $\Delta N$ information of the nutritional substances which is defined as changes in nutritional, organoleptic and aesthetic value of the nutritional substances after conditioning the nutritional substance, and (b) various conditioning protocols referenced to the nutritional substances;
   using an optical sensor, identifying values of a particular nutritional substance to be conditioned and retrieving information from the nutritional substance database related to the particular nutritional substance;
   receiving, via a consumer interface, input data from a consumer regarding a desired nutritional, organoleptic or aesthetic value of the particular nutritional substance after conditioning of the particular nutritional substance;
   receiving, via a controller, the input data from the consumer, and $\Delta N$ information for the particular nutritional substance, and based on the input data and $\Delta N$ information, retrieving and modifying a conditioning protocol comprising one of the various conditioning protocols stored in the nutritional substance database, the modified conditioning protocol comprising instructions for carrying out conditioning the particular nutritional substance to achieve the desired nutritional, organoleptic or aesthetic value of the particular nutritional input by the consumer wherein the modified conditioning protocol is responsive to a directly measured internal temperature of the nutritional substance; and
   cooking the nutritional substance responsive to the modified conditioning protocol including by modifying the conditioning parameters during cooking based on the directly measured internal temperature of the nutritional substance, and wherein the conditioning parameters comprise various time and temperatures for cooking the nutritional substance.

2. A method of dynamically conditioning a nutritional substance according to claim 1 wherein the conditioning protocols are further modified by at least one of a consumer observed nutritional, organoleptic, and aesthetic value observed of the nutritional substance and transmitted to a controller of a conditioner or to the dynamic nutritional substance database.

3. A method of dynamically conditioning a nutritional substance according to claim 1 wherein source information and at least one of a consumer desired nutritional, organoleptic, and aesthetic value after conditioning is transmitted to a nutritional substance consumer database or a dynamic nutritional substance database.

* * * * *